United States Patent
Ceder et al.

(10) Patent No.: US 7,292,958 B2
(45) Date of Patent: Nov. 6, 2007

(54) SYSTEMS AND METHODS FOR PREDICTING MATERIALS PROPERTIES

(75) Inventors: Gerbrand Ceder, Wellesley, MA (US);
Chris Fischer, Somerville, MA (US);
Kevin Tibbetts, Winchester, MA (US);
Dane Morgan, Madison, WI (US);
Stefano Curtarolo, Durham, NC (US)

(73) Assignee: Massachusetts institute of Technology, Cambridge, MA (US)

( * ) Notice: Subject to any disclaimer, the term of this patent is extended or adjusted under 35 U.S.C. 154(b) by 0 days.

(21) Appl. No.: 11/122,942

(22) Filed: May 4, 2005

(65) Prior Publication Data

US 2006/0074594 A1 Apr. 6, 2006

Related U.S. Application Data

(60) Provisional application No. 60/612,241, filed on Sep. 22, 2004.

(51) Int. Cl.
*G06F 11/30* (2006.01)
*G21C 17/00* (2006.01)
*G01N 31/00* (2006.01)

(52) U.S. Cl. ........................................ 702/182; 702/27

(58) Field of Classification Search ................. 702/182
See application file for complete search history.

(56) References Cited

U.S. PATENT DOCUMENTS

| | | | |
|---|---|---|---|
| 6,647,342 B2 * | 11/2003 | Iglesia et al. ................. | 702/22 |
| 2002/0123848 A1 * | 9/2002 | Schneiderman et al. ...... | 702/27 |
| 2004/0067529 A1 * | 4/2004 | Goodman et al. ........... | 435/7.1 |
| 2004/0230411 A1 * | 11/2004 | Zheng et al. .................. | 703/6 |

* cited by examiner

*Primary Examiner*—Michael Nghiem
(74) *Attorney, Agent, or Firm*—Hiscock & Barclay, LLP; Joseph B. Milstein

(57) ABSTRACT

Systems and methods for predicting features of materials of interest. Reference data are analyzed to deduce relationships between the input data sets and output data sets. Reference data includes measured values and/or computed values. The deduced relationships can be specified as equations, correspondences, and/or algorithmic processes that produce appropriate output data when suitable input data is used. In some instances, the output data set is a subset of the input data set, and computational results may be refined by optionally iterating the computational procedure. To deduce features of a new material of interest, a computed or measured input property of the material is provided to an equation, correspondence, or algorithmic procedure previously deduced, and an output is obtained. In some instances, the output is iteratively refined. In some instances, new features deduced for the material of interest are added to a database of input and output data for known materials.

47 Claims, 10 Drawing Sheets

SYSTEMS AND METHODS FOR PREDICTING MATERIALS PROPERTIES

CROSS-REFERENCE TO RELATED APPLICATIONS

This application claims priority to and the benefit of co-pending U.S. provisional patent application Ser. No. 60/612,241, filed Sep. 22, 2004, which application is incorporated herein by reference in its entirety.

STATEMENT REGARDING FEDERALLY FUNDED RESEARCH OR DEVELOPMENT

This invention was made with government support awarded by the Department of Energy under Grant Number DE-FG02-96ER45571. The government has certain rights in the invention.

FIELD OF THE INVENTION

The invention relates to calculations of materials properties in general and particularly to computational methods that employ a combination of databases and algorithmic methods.

BACKGROUND OF THE INVENTION

Ab-initio calculations, using quantum mechanical principles to calculate properties of materials, have been used for some time to predict features of materials. However, such calculations do not make use of the wealth of computed and measured information obtained on materials, in studying a system that has not previously been investigated or for which certain compositions or properties have not been investigated.

Prior to this work, no algorithms to extract knowledge and mathematical rules from the body of existing data on solid materials have been identified, limiting the usefulness of such data in predicting unknown properties of materials. Only simple heuristic models currently exist, in which visual correlations between properties, or few-parameter fits with pre-conceived (and therefore limited) models, are used to make predictions. Examples of heuristic models are Miedema's rules for compound formation in alloys, or Pettifor maps for making predictions of the structure of a new binary compound.

A number of problems in trying to predict structure information about new compounds have been observed, including difficult and time consuming calculations in ab-initio methods, and difficulties in extracting rules for use in heuristic models.

There is a need for systems and methods that combine information already known in a mathematical framework which can either predict directly attributes of materials or points at a few ab-initio calculations, which, when performed, will give the attribute of interest for the material.

SUMMARY OF THE INVENTION

In one aspect, the invention relates to a method for predicting a structure of an inorganic material of interest. The method comprises the following steps. For an inorganic material of interest different from an inorganic reference material, the method comprises the steps of selecting the inorganic material of interest, obtaining for the inorganic material of interest an initial value, the initial value being a selected one of a computed initial value and a measured initial value of at least one parameter of the inorganic material of interest, the initial value differing from a descriptor of an element present in the inorganic material of interest, providing the initial value of the at least one parameter for the inorganic material of interest to a computational procedure, computing with the computational procedure to obtain a result, and deducing a candidate structure of the inorganic material of interest based on the result, whereby data is generated to predict the structure of the inorganic material of interest. The computational procedure is a selected one of a computation that obtains a relationship between a known structure of at least one known inorganic reference material and a known initial value of a parameter of the at least one known inorganic reference material and that applies the relationship to the initial value of the at least one parameter for the inorganic material of interest, and a computation that compares the initial value of the at least one parameter for the inorganic material of interest with a known value of a corresponding parameter of the at least one known inorganic reference material, and that applies the comparison to a structural parameter of the known reference material.

In one embodiment, the obtaining step includes obtaining an additional initial value of at least one parameter of the inorganic material of interest, the additional initial value comprises a descriptor of an element present in the inorganic material of interest. In one embodiment, the method further comprises the optional step of computing a new parameter value for the candidate structure of the inorganic material of interest. In one embodiment, the method further comprises the optional step of, as necessary, iteratively performing the steps of providing the initial value of the at least one parameter for the inorganic material of interest wherein the new computed parameter is substituted for the initial value, deducing a candidate structure of the inorganic material of interest, and computing yet another new parameter value for the candidate structure.

In one embodiment, the step of iteratively performing the steps of providing, deducing, and computing is terminated when a metric relating to an incremental change of the parameter of the inorganic material of interest is less than a predefined difference. In one embodiment, at least one of the steps of providing, computing, and deducing is performed in a computational system comprises a programmed computer. In one embodiment, the computational system comprises a programmed computer further comprises a computer program containing an algorithm. In one embodiment, the computational system comprises a programmed computer further comprises a knowledge machine. In one embodiment, the inorganic material of interest comprises a plurality of inorganic materials. In one embodiment, the inorganic reference material comprises a plurality of materials. In one embodiment, the initial value of the inorganic material of interest comprises a plurality of initial values for a plurality of parameters of the inorganic material of interest. In one embodiment, the initial value of the parameter of the inorganic reference material comprises a plurality of initial values for a plurality of parameters of the inorganic reference material. In one embodiment, the known value of the parameter of the inorganic reference material comprises at least one machine-readable datum. In one embodiment, the at least one machine-readable datum comprises an element of a database. In one embodiment, the structure is characterized uniquely. In one embodiment, the structure is partially described. In one embodiment, the structure comprises a selected one of a charge density, a structural property, a parameter of a crystal structure, a parameter of a non-crystalline structure, a symmetry of a structure, a space group, a point group, an electronic structure property, and a quantity calculable from one or more of a quantum-mechanical ground state, a quantum mechanical excited state, and a generalized thermodynamic susceptibility of the inorganic material of interest. In one embodiment, the prediction of the structure of the inorganic material of interest comprises a prediction that the inorganic material of interest is not stable under a defined condition. In one embodiment, the structure is a function of temperature. In one embodiment, the structure is a function of pressure. In one embodiment, the structure is a function of volume. In one embodiment, the structure is a function of a thermodynamic field or a thermodynamic force. In one embodiment, the structure is a function of chemical composition. In one embodiment, the step of computing comprises applying a computational method involving a selected one or more of a partial least square (PLS) method, a Principal Component Analysis (PCA) method, a data mining method, a knowledge discovery method, a visualization method, a statistical method, a regression method, a linear regression method, a non-linear regression method, a Bayesian method, a clustering method, a neural network method, a support vector machine method, a decision tree method, and a cumulant expansion.

In another aspect, the invention features a method for predicting a property of an inorganic material of interest. The method comprises the following steps. For an inorganic reference material, the steps of selecting an input data set and an output data set wherein the output data set is a subset of the input data set, and identifying a computational procedure that generates a member of the output data set when a member of the input data set comprises an initial value of a parameter of the inorganic reference material is used as input. For an inorganic material of interest different from the inorganic reference material, the steps of selecting the inorganic material of interest, obtaining for the inorganic material of interest an initial value, the initial value being a selected one of a computed initial value and a measured initial value of at least one parameter of the inorganic material of interest, providing the initial value of the at least one parameter for the inorganic material of interest to the computational procedure, computing with the computational procedure to obtain a result, and deducing a candidate property of the inorganic material of interest based on the result, whereby data is generated to predict the property of the inorganic material of interest.

In one embodiment, the method further comprises the optional step of computing a new parameter value for the candidate property of the inorganic material of interest. In one embodiment, the method further comprises the optional step of, as necessary, iteratively performing the steps of providing the initial value of the at least one parameter for the inorganic material of interest wherein the new computed parameter is substituted for the initial value, deducing a candidate property of the inorganic material of interest, and computing yet another new parameter value for the candidate property. In one embodiment, the step of iteratively performing the steps of providing, deducing, and computing is terminated when a metric relating to an incremental change of the parameter of the inorganic material of interest is less than a predefined difference. In one embodiment, at least one of the steps of providing, computing and deducing is performed in a computational system comprises a programmed computer. In one embodiment, the computational system comprises a programmed computer further comprises a computer program containing an algorithm. In one embodiment, the computational system comprises a programmed computer further comprises a knowledge machine. In one embodiment, the initial value of the parameter for the inorganic material of interest and the initial value of the parameter for the inorganic reference material are parameters that describe a corresponding material feature. In one embodiment, the inorganic material of interest comprises a plurality of inorganic materials. In one embodiment, the inorganic reference material comprises a plurality of materials. In one embodiment, the initial value of the inorganic material of interest comprises a plurality of initial values of the inorganic material of interest. In one embodiment, the initial value of the parameter of the inorganic reference material comprises a plurality of initial values for a plurality of parameters of the reference material. In one embodiment, the initial value of the parameter of the inorganic reference material comprises at least one machine-readable datum. In one embodiment, the at least one machine-readable datum comprises an element of a database. In one embodiment, at least one of the initial values of the inorganic material of interest and the predicted property of the inorganic material of interest is added to the database. In one embodiment, the property comprises a selected one of an energy, a charge density, a structural property, a parameter of a crystal structure, a parameter of a non-crystalline structure, a symmetry of a structure, a space group, a point group, an optical property, an electromagnetic property, a mechanical property, a quantum-mechanical property, an electronic structure property, a thermodynamic property, a magnetic property, and a quantity calculable from one or more of a quantum-mechanical ground state, a quantum mechanical excited state, and a generalized thermodynamic susceptibility of the inorganic material of interest. In one embodiment, the prediction of the property of the inorganic material of interest comprises a prediction that the inorganic material of interest is not stable under a defined condition. In one embodiment, the property is a function of temperature. In one embodiment, the property is a function of pressure. In one embodiment, the property is a function of volume. In one embodiment, in one embodiment, the property is a function of a thermodynamic field or a thermodynamic force. In one embodiment, the property is a function of chemical composition. In one embodiment, the step of computing comprises applying a computational method involving a selected one or more of a partial least square (PLS) method, a Principal Component Analysis (PCA) method, a data mining method, a knowledge discovery method, a visualization method, a statistical method, a regression method, a linear regression method, a non-linear regression method, a Bayesian method, a clustering method, a neural network method, a support vector machine method, a decision tree method, and a cumulant expansion.

In one aspect, the invention relates to a method for predicting a property of an inorganic material of interest. The method comprises the steps of, for an inorganic material of interest different from an inorganic reference material, selecting the inorganic material of interest; obtaining for the inorganic material of interest an initial value, the initial value being a selected one of a computed initial value of at least one parameter or attribute for at least one proposed feature of the inorganic material of interest and a measured initial value of at least one parameter for a known feature of the inorganic material of interest; providing the initial value of the at least one parameter for the inorganic material of interest and a selected one of a computed parameter of the reference material and a measured parameter of the reference material to a computational procedure to obtain a result; deducing a candidate feature or value of an attribute of the inorganic material of interest based on the result; optionally computing a new parameter value for the candidate feature of the inorganic material of interest; and optionally, as necessary, iteratively performing the steps of providing the initial value of the at least one parameter for the inorganic material of interest wherein the new computed parameter is substituted for the initial value, deducing a candidate feature of the inorganic material of interest, and computing yet another new parameter value for the candidate feature; whereby a suitable amount of data is generated to predict the property of the inorganic material of interest.

In one embodiment, the computed parameter for the inorganic material of interest and the selected parameter for the reference material are parameters of the same type. In one embodiment, at least one of the steps of providing, deducing and computing is performed in a computational system comprising a programmed computer. In one embodiment, the computational system comprising a programmed computer further comprises a computer program containing an algorithm. In one embodiment, the computational system comprising a programmed computer further comprises a knowledge machine. In one embodiment, the inorganic material of interest comprises a plurality of inorganic materials. In one embodiment, the reference material comprises a plurality of materials. In one embodiment, the initial value of the inorganic material of interest comprises a plurality of initial values of the inorganic material of interest. In one embodiment, the selected one of the computed parameter of the reference material and the measured parameter of the reference material comprises a plurality of parameters of the reference material. In one embodiment, the selected one of the computed parameter of the reference material and the measured parameter of the reference material comprises at least one machine-readable datum. In one embodiment, the at least one machine-readable datum comprises an element of a database. In one embodiment, the property comprises a selected one of an energy, a charge density, a parameter of a crystal structure, a space group, a point group, an optical property, an electromagnetic property, a mechanical property, a quantum-mechanical property, an electronic structure property, a thermodynamic property, a magnetic property, and a quantity calculable from a quantum-mechanical ground state or generalized thermodynamic susceptibility of the inorganic material of interest. In one embodiment, the prediction of the property of the inorganic material of interest comprises a prediction that the inorganic material of interest is not stable under a defined condition. In one embodiment, the proposed feature is a function of temperature. In one embodiment, the proposed feature is a function of pressure. In one embodiment, the proposed feature is a function of a thermodynamic field or a thermodynamic force. In one embodiment, the proposed feature is a function of chemical composition. In one embodiment, the step of iteratively performing the steps of providing, deducing, and computing is terminated when a metric relating to an incremental change of the parameter of the inorganic material of interest is less than a predefined difference. In one embodiment, the step of computing comprises applying a computational method involving a selected one of a partial least squares (PLS) method, a Principal Component Analysis (PCA) method, a data mining method, a knowledge discovery method, a visualization method, a statistical method, a regression method, a linear regression method, a non-linear regression method, a Bayesian method, a clustering method, a neural network method, a support vector machine method, a decision tree method, and a cumulant expansion.

In one aspect, the invention relates to a method for generating a computational procedure applicable to predicting a property of an inorganic material of interest. The method comprises the steps of based on a selected one of an experimentally measured datum and a calculated datum for a reference material, deducing a mathematical relationship that employs parameters descriptive of the datum; and generating a computational procedure based on the mathematical relationship, the computational procedure employing a representation of the mathematical relationship that is other than a visual representation, the computational procedure comprising at least one computational step, the computational procedure useful to predict a property of a inorganic material of interest. In one embodiment, the mathematical relationship can be selected to have optimal predictive power.

In one embodiment, the method further comprises the step of applying the computational procedure to predict a property of the inorganic material of interest. In one embodiment, the method further comprises the step of adding the property of the inorganic material of interest to a database. In one embodiment, the method further comprises the step of refining the computational procedure based on the contents of the database after the addition of the property of the inorganic material of interest to the database.

In another aspect, the invention relates to a method for generating a computational procedure applicable to predicting a property of an inorganic material of interest. The method comprises the steps of based on a selected one of an experimentally measured datum and a calculated datum for a reference material, deducing a mathematical relationship that employs parameters descriptive of the datum; and generating a computational procedure based on the mathematical relationship, the computational procedure comprising at least one computational step, the computational procedure employing a representation of the inorganic material using a combination of at least two chemical elements as an independent variable of the representation, the computational procedure useful to predict a property of a inorganic material of interest.

In one embodiment, the method further comprises the step of applying the computational procedure to predict a property of the inorganic material of interest. In one embodiment, the method further comprises the step of adding the property of the inorganic material of interest to a database. In one embodiment, the method further comprises the step of refining the computational procedure based on the contents of the database after the addition of the property of the inorganic material of interest to the database.

In yet another aspect, the invention relates to a method of predicting at least one candidate structure for a compound not known to exist comprising at least two chemical elements. The method comprises the steps of employing as input a selected one of known information about at least one stable structure in a chemical system comprising the at least two chemical elements and a calculated energy of a proposed structure in the chemical system comprising the at least two chemical elements; providing the input to a computational element operating a selected one of an algorithm and a knowledge machine; and calculating the at least one candidate structure for the compound comprising the at least two chemical elements.

In one embodiment, the method further comprises repetition of the steps of employing as input a selected one of known information, providing the input to a computational element, and calculating at least one additional candidate structure, whereby a plurality of predicted candidate structures is generated as output. In one embodiment, the list of predicted candidate structures comprises fewer than 20 structures. In one embodiment, a probability exceeds 90% that the correct structure for the compound comprising the at least two chemical elements is present in the list of predicted candidate structures. In one embodiment, the algorithm or knowledge machine is derived by applying a data mining algorithm on a database of computed energies of at least one crystal structure in at least one materials system. In one embodiment, the data mining algorithm is an algorithm involves a selected one of a partial least square (PLS) method, a Principal Component Analysis (PCA) method, a data mining method, a knowledge discovery method, a visualization method, a statistical method, a regression method, a linear regression method, a non-linear regression method, a Bayesian method, a clustering method, a neural network method, a support vector machine method, a decision tree method, and a cumulant expansion. In one embodiment, the data mining algorithm is exercised on a database of experimentally identified crystal structures. In one embodiment, the database of experimentally identified crystal structures is a selected one of a Crystmet database, an ICSD database, and a Pauling File. In one embodiment, the algorithm or knowledge machine is derived by applying a data mining algorithm on a database of measured energies of at least one crystal structure in at least one materials system.

In a still further aspect, the invention relates to a computer program recorded on a machine-readable medium, the computer program configured to predict a property of the inorganic material of interest. The computer program comprises a selection module for selecting a inorganic material of interest different from an inorganic reference material; an estimation module that provides an initial value for the inorganic material of interest, the initial value being a selected one of a computed initial value of at least one parameter for at least one proposed feature of the inorganic material of interest and a measured initial value of at least one parameter for a known feature of the inorganic material of interest; a calculation module that receives the initial value of the at least one parameter for the inorganic material of interest and a selected one of a computed parameter of the reference material and a measured parameter of the reference material and that calculates a result; a state deducing module that deducing a candidate feature of the inorganic material of interest based on the result; and a computation module that computes a new parameter value for the candidate feature of the inorganic material of interest.

In one embodiment, the computer program further comprises an iteration module that, optionally, as necessary, iteratively command the performance of the steps of receiving the initial value of the at least one parameter for the inorganic material of interest wherein the new computed parameter is substituted for the initial value, deducing a candidate feature of the inorganic material of interest, and computing yet another new parameter value for the candidate feature, so as to provide an improved prediction of the property of the inorganic material of interest. In one embodiment, the computer program further comprises a data storage module that controls the recording of the predicted property of the inorganic material of interest in a database. In one embodiment, the computer program further comprises a data retrieval module that controls the retrieval of data from a database.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

Figure 1:
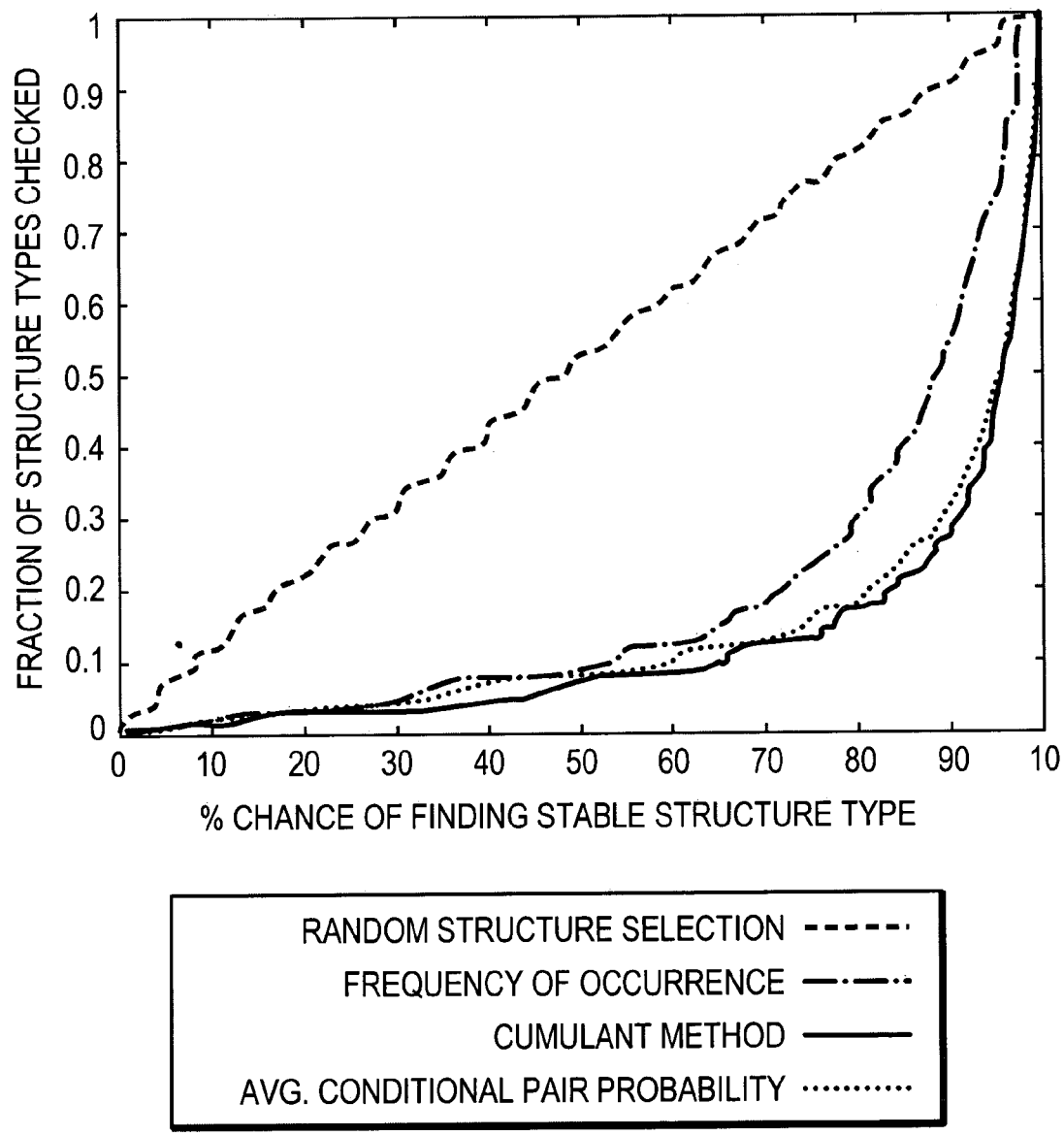
FIG. 1 is a diagram showing prediction test results, according to principles of the invention.

The invention relates to systems and methods that utilize information in databases to provide guidance in selecting algorithmic methods of computation, and that generate information that is introduced into one or more databases so as to inform subsequent calculations, by which combination both the algorithmic methods are improved and the likelihood of obtaining correct results of calculation are also improved. In the present description, the systems and method of the invention are applied to chemical systems for prediction of the existence (or non-existence) of compounds and for prediction of the structures of compounds found to exist. The systems and methods of the invention provide efficient, cost-effective, and expeditious procedures for making assessments of features, properties and attributes of materials of interest when compared to experimental methods, in which a material of interest is first synthesized, and the features, properties and attributes are then measured. The information provided by the systems and methods of the invention can provide guidance in selecting a material to synthesize, based on the predicted features, properties and attributes.

According to systems and methods of the invention, one must distinguish between "computed" values (or alternatively, "calculated" values) and "measured" values for parameters or features of compounds. As used herein, the term "computed," as in "computed value," is intended to denote a value that is primarily derived from theory and computation, with limited experimental input. For example, a computed value is often obtained for a composition of matter that is not known to exist, or that has not been synthesized, and that is postulated or modeled, without a physical substance upon which a measurement can be performed. In contradistinction, a measured value is a value that is obtained by making one or more measurements on a real, physical substance, possibly with further mathematical manipulation of the results of the measurement, but clearly based upon one or more measurements that are actually performed. In some instances, a computed value can be obtained for comparison with a measured value, for example to confirm that the computational method that produces the computed value yields quantities that closely represent the value actually measured (e.g., to validate the computational tool as being reliable, rather than to obtain a value which is also available by experimental procedures on a real, physical substance).

For the purposes of this description, the following terms are defined, in keeping with the generally accepted usage in the field of study of inorganic materials in the liquid and solid states. A "system" is understood to denote a plurality of elements. A binary system denotes a system with two elements, a ternary system has three elements, and so on for additional numbers of elements. A system can often be represented diagrammatically, using such parameters as composition, temperature, pressure, and volume. Sometimes we also refer to a system as an alloy, or as a mixture. A "structure" (or crystal structure) denotes a specific structure, such as a crystallographic structure that can be described in terms of a unit cell, taken on by a system at a particular composition of the system under defined temperature and pressure. A crystallographic structure can be measured for a real structure (as opposed to a computed or calculated structure) by methods such as x-ray diffraction. It is to be understood that it is possible to have multiple structures in a system as one or more of the composition, the temperature, and/or the pressure varies. A "compound" refers to a system at a given composition, corresponding to the exact stoichiometry of the structure. In general, a compound may be thought of as a specific composition that is thermodynamically stable under some set of conditions of composition, temperature and pressure. As is known in the art, a compound may be referred to by a formula, such as $A_2B_3$ or $A_3B$, where A and B represent the chemical symbols of elements. The structure of a composition may also be referred to using a compound as a descriptor, using a nomenclature for a prototypical composition having the same or an isomorphic structure. As an example, many materials take on the sodium chloride, or NaCl, cubic structure. In addition, or alternatively, structures are also identified by space group and/or point group notation. While every compound does have a structure, the term compound typically does not include or connote crystal structure information. As is also well understood, for a specified composition, temperature and pressure, it may be that no stable compound exists, and correspondingly, no crystal structure is defined, or that a plurality of defined compounds and/or elements may coexist. All of the concepts presented in the above paragraph are well known and commonly used in the description of materials using phase diagrams.

The systems of the invention utilize, and the methods of the invention are carried out with, programmable computers and associated computer programs that are recorded on machine-readable media. The computers and software are in general (but are not required to be) part of computer systems, which can include computers having size and capacity ranging from hand held computational devices to supercomputers. In addition, the computers and software can interface with commonly used input/output devices (such as keyboards, pointing devices, touch screens, video screens, printers, speakers and enunciators), memory and/or storage devices (such as semiconductor, optical, and magnetic memory devices), communication devices (such as modems, networks, and commonly used hard-wired and wireless electronic communication media), and resources in both local and remote locations (such as databases and compendia of electronically accessible published information).

In describing the systems and methods of the invention, definitions for certain additional terms are useful. As used herein, the term "material of interest" is intended to denote a material one wishes to study or to make predictions about. As used herein, the term "reference material" is intended to denote any known material that appears as an entry in a database, or that is otherwise described in an electronically accessible medium or in a paper copy reference work, from which the information is transferred to a computing file for the purpose of the methods described in this work. A known material can be a physical material that has been prepared and studied, or a material studied in theoretical terms for which some characteristic, property, parameter or physical state has been calculated or computed. As used herein, the term "feature," such as in the usage "a feature of a material," is intended to denote a generalization that includes a physical state of a material, and any characteristic, property, or parameter of a material. As used herein, for the purposes of the examples given to describe the invention, the term "material" is intended to denote any of condensed matter, solid state material, crystalline material, and inorganic material. It is further contemplated that the kinds of systems and methods described herein may find useful application in studying substances other than those denoted as "materials" herein.

The description of the systems and the methods of the invention are described with respect to several examples.

EXAMPLE 1

Using a Database of Experimentally Measured Crystal Structures to Predict Unknown Structures Several large experimental databases comprising thermodynamic data of alloy systems are now available. In one embodiment, the invention relates to methods that enable one to use these databases to build algorithms, which then in turn can be used to predict structures or material attributes not in the database. In this example, a cumulant expansion is built from a database of experimentally measured crystal structures. The cumulant expansion then gives with high accuracy candidate structures for systems that were not included in building the cumulant expansion. As such the method can predict structure for compounds in new systems or systems that are only partially characterized.

Extracting and Processing the Data:

In one embodiment, data was extracted from the Pauling File Inorganic Materials Database, Binaries Edition, Version 1.0. There are 28,457 structure type listings in this database. In this database, a listing includes prototype name, alloy system, formula and modifier (high temperature, high pressure), among other things (space group number, Pearson symbol, etc.).

In the present example, we are interested in looking at stable structure types at low temperature and pressure, so we have removed all listings identified by the Pauling File as high temperature or high pressure.

We determine a set of allowed compositions for each structure type, based on the distribution of entries for that structure type. Next we assign each of these composition to the nearest rational fraction, out of a set of fractions that includes the following:

| | | | | | |
|---|---|---|---|---|---|
| 0% | 10% (1/10) | 16.7% (1/6) | 20% (1/5) | 22% (2/9) | 25% (1/4) |
| 28.6% (2/7) | 30% (3/10) | 33.3% (1/3) | 37.5% (3/8) | 40% (2/5) | 42.9% (3/7) |
| 44.4% (4/9) | 50% (1/2) | 55.6% (5/9) | 57.1% (4/7) | 60% (3/5) | 62.5% (5/8) |
| 66.7% (2/3) | 70% (7/10) | 71.4% (5/7) | 75% (3/4) | 77.8% (7/9) | 80% (4/5) |
| 83.3% (5/6) | 85.7% (6/7) | 90% (9/10) | 100% | | |

This discretization (or binning) of compositions is performed to improve the statistics. The methods described herein are not limited to these compositions. After binning the listings into this set of compositions, we remove all duplicate entries. Two entries are considered to be duplicates if they have the same prototype name, composition and alloy system.

We have extracted a subset of the data in order to compare similar alloys. We are using entries for alloy systems that do not contain any non-metals, defined as the elements He, B, C, N, O, F, Ne, Si, P, S, Cl, Ar, As, Se, Br, Kr, Te, I, Xe, At, and Rn. This subset of the data contains 4,836 entries. The method can be extended to include alloys including these non-metals.

Statistics:

We have calculated some statistics for this dataset in order to evaluate the predictive ability of the data. First we define some variables. In general, $c_i$ and $c_j$ are fractions in the range of $0.0 < c_i, c_j < 1.0$.

$N_{\alpha(i)}$=Number of unique entries for structure type alpha at composition $c_i$.

$N_{\alpha(i)\beta(j)}$=Number of systems with structure type alpha at composition $c_i$ and structure type beta at composition $c_j$.

We can improve the statistics by considering the symmetry of the data. The only difference between structure type $\alpha$ at composition $c_i$ and structure type $\alpha$ at composition $1-c_i$ is how the system is defined. That is to say that the system A-B at composition $c_i$ in A can be represented as $A(c_i)$–$B(1-c_i)$, e.g., $c_i$ percent element A and $(1-c_i)$ percent element B. In the statistical analysis we combine the statistics to include the symmetric equivalent structure type or pair of symmetric equivalent structure types.

Conditional Pair Probabilities:

The conditional pair probability is defined as the probability that structure type $\beta$ appears in a system in which structure type $\alpha$ appears. This is the ratio of the number of times the two structures appear in the same system to the number of times structure type $\alpha$ appears.

$$P(\beta(j)|\alpha(i)) = N_{\alpha(i)\beta(j)} / N_{\alpha(i)}$$

These pair probabilities embed information about correlation between the appearance of various structures and can be used to predict structure. The use of pair correlations in this example should be seen in no way as a limitation to pair correlations. Higher order correlations, such as the occurrence of three crystal structures together in one alloy can also be used if sufficient data is available. The conditional pair probabilities are collected based on all the data in the previously defined dataset which is extracted from the Pauling files.

Cumulant Expansion:

A cumulant expansion is built to give the model predictive power. A cumulant expansion is a decomposition of a probability mass function into smaller parts. Cumulant expansions are described in the appended document entitled "Coarse-Graining and Data Mining Approaches to the Prediction of Structures and their Dynamics," which was filed as part of the disclosure of U.S. Ser. No. 60/612,241, the entire disclosure of which has been incorporated herein by reference. When no approximations are applied, a cumulant expansion is an exact representation of the full probability mass function. The exemplary method described herein determines the probability that some structures occur together in a new system of interest, from the limited information known about that new system, and the pair correlation determined from the Pauling file database. For example, given that two structures are known in the new system, the pair correlations from the Pauling files can be used to find which other crystal structures may occur in conjunction with these two structures. The cumulant expansion is a mathematical way to calculate proper probabilities for crystal structure to appear in a system, consistent with the structures already known about the system.

We define the term "event" to mean that $\alpha(c_i)$=TRUE when structure type alpha is present at composition $c_i$ in an alloy system.

An alloy system in a database can be represented as the logical conjunction of each of the individual events comprising the system (i.e., the logical conjunction of events is true for that particular system and any others which list the same structure types at the same compositions).

A measure of the predictive nature of this method is its ability to predict what structure type will appear at a composition given that everything else about the system in question is known. To generate a list of candidate structures we will compute the quantity $p(\beta(c_i)|\alpha(c_1), \ldots, \alpha(c_n))$ which can be read as: "the probability of structure $\beta(c_i)$ given that structures $\alpha(c_1)$ through $\alpha(c_n)$ have appeared." Ranking the candidate structures $\{\beta(c_i)\}$ is based on this probability. The conditional probability can be represented approximately as a cumulant expansion in which only terms including up to two events are retained:

To determine the cumulant expansion, one first collects all known stable structure types for a system of interest. We identify these as structure types $\alpha_1, \alpha_2 \ldots \alpha_n$ at compositions $c_1, c_2, \ldots c_n$. We compute the probability that structure $\beta$ is present at composition $c_i$ as follows:

$$p(\beta(c_i)|\alpha(c_1), \ldots, \alpha(c_n)) \approx [p(\beta(c_i))]^{1-n} \prod_{j=1}^{n} p(\beta(c_i)|\alpha(c_j)) \quad (1)$$

Using a Bayesian estimate for each conditional probability Equation 1 reduces to:

$$p(\beta(c_i)|\alpha(c_1), \ldots, \alpha(c_n)) \approx p(\beta(c_i))\prod_{j=1}^{n} p(\beta(c_i)|\alpha(c_j)) \quad (2)$$

Each probability/conditional probability appearing on the right hand side of Equation 1 can be calculated with Laplace's rule of succession: and $$p(\beta(c_i)) = \frac{N_{\beta(c_i)}+1}{N_{sys}+2} \text{ and } p(\beta(c_i)|\alpha(c_j)) = \frac{N_{\beta(c_i),\alpha(c_j)}+1}{N_{\alpha(c_j)}+2}.$$

Prediction Tests:

We performed a set of prediction tests using the experimental database to assess how well the prediction test operates. To simulate a prediction we leave out, or deliberately omit, one alloy system from the dataset used to build the cumulant information. A prediction was made for every structure of the omitted system using two different algorithms described herein. Each of these methods includes creating a list of the structure types that could appear at the composition of interest, ordered by a different, selected, criterion. For each structure type prediction we leave out all entries from the alloy system of the entry we are trying to predict when determining the statistics for that test. To assess the efficiency of these novel algorithms, they are compared to two commonly used approaches.

The first commonly used approach is to randomly pick structures as candidate structures. This is the method that contains the least (e.g., zero) information. We refer to this as the random method. A more informed approach is to rank structures based on the frequency with which they occur in the database. We call this method the frequency of occurrence method. Our two knowledge methods are the following: 1) For each structure type beta that could appear at the composition of interest, we determine the conditional pair probability for beta with each of the other structure types that appear in the system. We then average these conditional pair probabilities, and order the structure types by this average. We refer to this as the averaged conditional pair probability method. The second method is the cumulant method described above. The results of this test are shown in FIG. 1. FIG. 1 is a diagram that shows the fraction of structure types that one expects would need to be investigated for a given percentage chance of finding the correct structure type. In FIG. 1, the curves representing each method of interest are indicated by the key in the upper left. The cumulant method gives the best results, slightly better than average conditional pair probability. This shows one way to determine the best prediction techniques. Both our knowledge methods are significantly better than either the random or frequency of occurrence method.

As an example of this technique consider alloy system Al—Pd. The Pauling File has 7 structure type entries for this system. They are presented in Table I as a function of composition.

TABLE I

| Structure Type | Composition (percent Al) |
|---|---|
| Cu | 0 |
| $Co_2Si$-b | 0.33 |
| FeSi | 0.5 |
| $Ni_2Al_3$ | 0.6 |
| $CaF_2$ | 0.667 |
| $Pt_8Al_{21}$ | 0.714 |
| Cu | 1 |

As a test of the method we assume we did not know the structure at composition 0.6 and see whether our method can predict it from the knowledge of the other structures. The six structures in the above table other than $Ni_2Al_3$ are structures $\alpha_1 \ldots \alpha_6$ for the statistical analysis. Tables II, III, and IV present the ranked lists of structure types with the frequency of occurrence method, averaged conditional pair probability method, and cumulant method.

For this example, the averaged conditional pair probability method ranks the structure $3^{rd}$ on a list of possible candidate structures, the cumulant method ranks it first, and the frequency of occurrence method results in a ranking of $7^{th}$ Ni2Al3 was ranked first by the cumulant method, and had a probability value with this method over three times as large as the second structure on the list, indicating the strength of cumulant method in predicting short list of very likely structures.

TABLE II

Frequency of Occurrence List

| Structure Type | Occurrences |
|---|---|
| (Cr0.49Fe0.51) | 24 |
| Er3Ni2 | 21 |
| U3Si2 | 16 |
| Y3Rh2 | 11 |
| Gd3Ga2 | 11 |
| Ca16Sb11 | 10 |
| Ni2Al3 | 9 |
| Cu5Zn8 | 6 |
| Zr3Al2 | 6 |
| Er3Ru2 | 6 |
| Zr7Ni10 | 5 |
| Gd3Al2 | 5 |
| Zr2Al3 | 4 |
| Li3Al2 | 3 |
| La2Ni3 | 3 |
| Dy3Ni2 | 3 |
| Sr2Sb3 | 3 |
| Pu31Pt20 | 3 |
| Ni3Sn2 | 3 |
| Mg2Cu | 3 |
| Ba5Si3 | 3 |
| Ni13Ga9 | 3 |
| K2Au3 | 2 |
| La2O3 | 2 |
| TaIr | 2 |
| Tl2Pt3 | 2 |
| Ru2Ge3 | 2 |
| Rb2In3 | 2 |
| Mg17Al12 | 2 |
| Ranking 7 | Fraction 0.241379310344828 |

TABLE III

Averaged Conditional Pair Probability List

| Structure Type | Normalized Avg. Conditional Pair Probability |
|---|---|
| Er3Ni2 | 0.163 |
| Y3Rh2 | 0.12 |
| Ni2Al3 | 0.108 |
| U3Si2 | 0.09 |
| (Cr0.49Fe0.51) | 0.072 |
| Gd3Al2 | 0.054 |
| Zr3Al2 | 0.048 |
| Gd3Ga2 | 0.036 |
| Ca16Sb11 | 0.036 |
| Cu5Zn8 | 0.036 |
| Dy3Ni2 | 0.036 |
| Zr7Ni10 | 0.03 |
| Er3Ru2 | 0.024 |
| Ni13Ga9 | 0.018 |
| Pu31Pt20 | 0.018 |
| TaIr | 0.018 |
| Zr2Al3 | 0.012 |
| Tl2Pt3 | 0.012 |
| Mg17Al12 | 0.012 |
| K2Au3 | 0.012 |
| Mg2Cu | 0.006 |
| Ba5Si3 | 0.006 |
| La2Ni3 | 0.006 |
| Sr2Sb3 | 0.006 |
| Ni3Sn2 | 0.006 |
| Li3Al2 | 0.006 |
| Ru2Ge3 | 0.006 |
| La2O3 | 0 |
| Rb2In3 | 0 |
| Ranking 3 | Fraction 0.103448275862069 |

TABLE IV

Cumulant Method List

| Structure Type | Normalized Cumulant Expansion |
|---|---|
| Ni2Al3 | 0.593207771 |
| Er3Ni2 | 0.167482327 |
| Y3Rh2 | 0.071184933 |
| (Cr0.49Fe0.51) | 0.060556627 |
| U3Si2 | 0.060507193 |
| Gd3Ga2 | 0.008898117 |
| Gd3Al2 | 0.008898117 |
| Zr3Al2 | 0.007266795 |
| Ca16Sb11 | 0.003806417 |
| Dy3Ni2 | 0.003163775 |
| Zr7Ni10 | 0.002966039 |
| Cu5Zn8 | 0.002422265 |
| Er3Ru2 | 0.001730189 |
| Pu31Pt20 | 0.001186416 |
| TaIr | 0.000889812 |
| Ni13Ga9 | 0.000790944 |
| Zr2Al3 | 0.00074151 |
| Tl2Pt3 | 0.000444906 |
| Mg17Al12 | 0.000444906 |
| K2Au3 | 0.000444906 |
| Mg2Cu | 0.000395472 |
| Ba5Si3 | 0.000395472 |
| La2Ni3 | 0.000395472 |
| Li3Al2 | 0.000395472 |
| Sr2Sb3 | 0.000395472 |
| Ni3Sn2 | 0.000395472 |
| Ru2Ge3 | 0.000296604 |
| La2O3 | 0.000148302 |
| Rb2In3 | 0.000148302 |
| Ranking 1 | Fraction 0.0344827586206897 |

EXAMPLE 2

Using a Library/Database of Calculated Energies of Structure in a Group of Binary Alloys Just as experimental information can be used to extract knowledge and formulate algorithms used for predicting the structure of new materials, calculated data can be used in the database. In this example, we show how knowledge extracted with Partial Least Square Methods (PLS) from a dataset of calculated structure energies, is used to predict likely structures in a new system. Every time a structure is suggested, its energy can be calculated, which in turn improves the accuracy of the prediction. Partial Least Squares methods are known in the art and are described briefly in the document entitled "Coarse-Graining and Data Mining Approaches to the Prediction of Structures and their Dynamics" and references therein, which was filed as part of the disclosure of U.S. Ser. No. 60/612,241, the entire disclosure of which has been incorporated herein by reference.

A database was constructed containing the calculated energy of 114 structure types in 55 binary alloys. The ground state energy of these structures was computed with Density Functional Theory in the Local Density Approximation as implemented in the Vienna Ab-Initio Simulation Package (VASP). The method is not limited to energies obtained with this package, but can be used with any model for calculating the energy of structures, including quantum mechanical approaches, semi-empirical approaches or empirical energy models.

In some embodiments, the PLS/knowledge extraction step is applied to data to select an algorithmic method for application.

Figure 2:
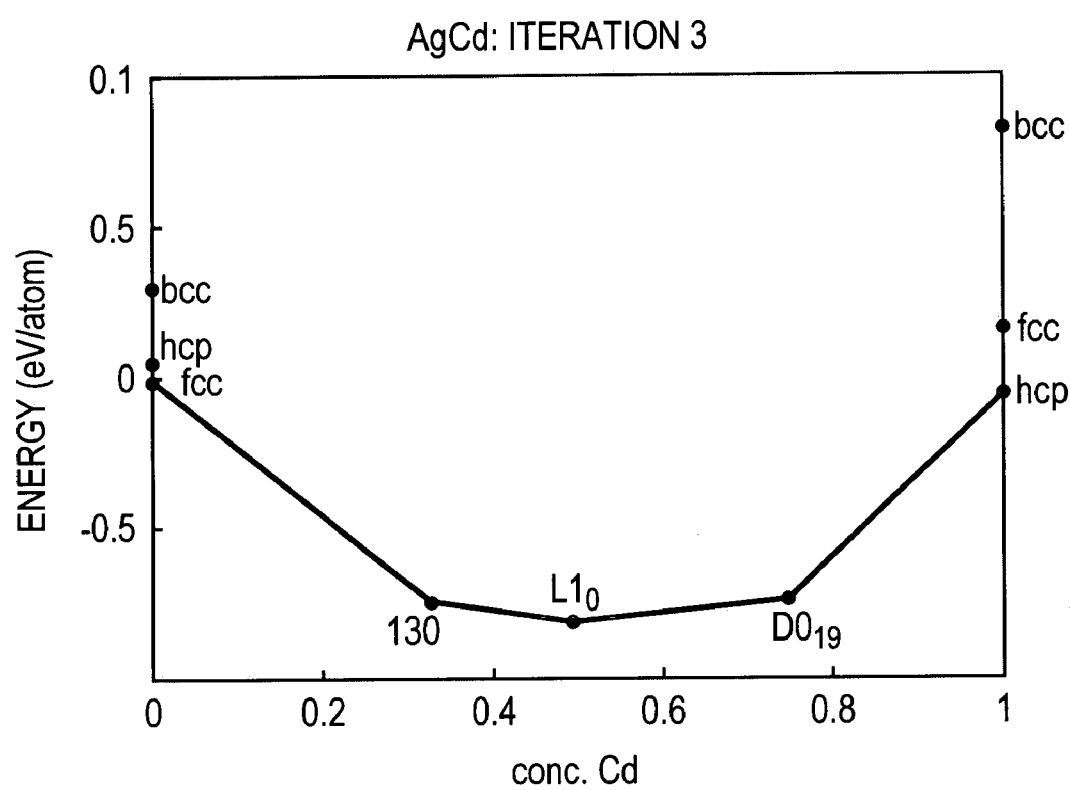
FIG. 2 shows the mixing energies as predicted by the algorithm for the Ag—Cd system at iteration 3, according to principles of the invention.

For a new system of interest, which is the Ag—Cd system in the present example, the algorithm is initialized with the calculated energies of pure elemental Ag and Cd in the fcc, bcc and hcp structures. In the first iteration, there is not enough information available for the Ag—Cd system to generate predictions from our algorithm. Hence the algorithm extracts a frequent structure prototype from the library and calculates its ab-initio energy. In this case, the suggested structure to calculate is $DO_{19}$. This is repeated in iteration 2 with a suggested structure of $Ll_0$. From iteration 3 on, the knowledge algorithm can be used to extract predictions from the database. In iteration 3, the PLS method is used to estimate the energy of all 114 structure types that have not been calculated yet for Ag—Cd. FIG. 2 shows the mixing energies as predicted by the algorithm for the Ag—Cd system at iteration 3. The algorithm suggest a new ground state structure at concentration C=33% labeled as "130." The label "130" refers to a label number in the database and is a structure with stoichiometry $A_4B_2$ and is a decoration of an hcp lattice.

Figure 3:
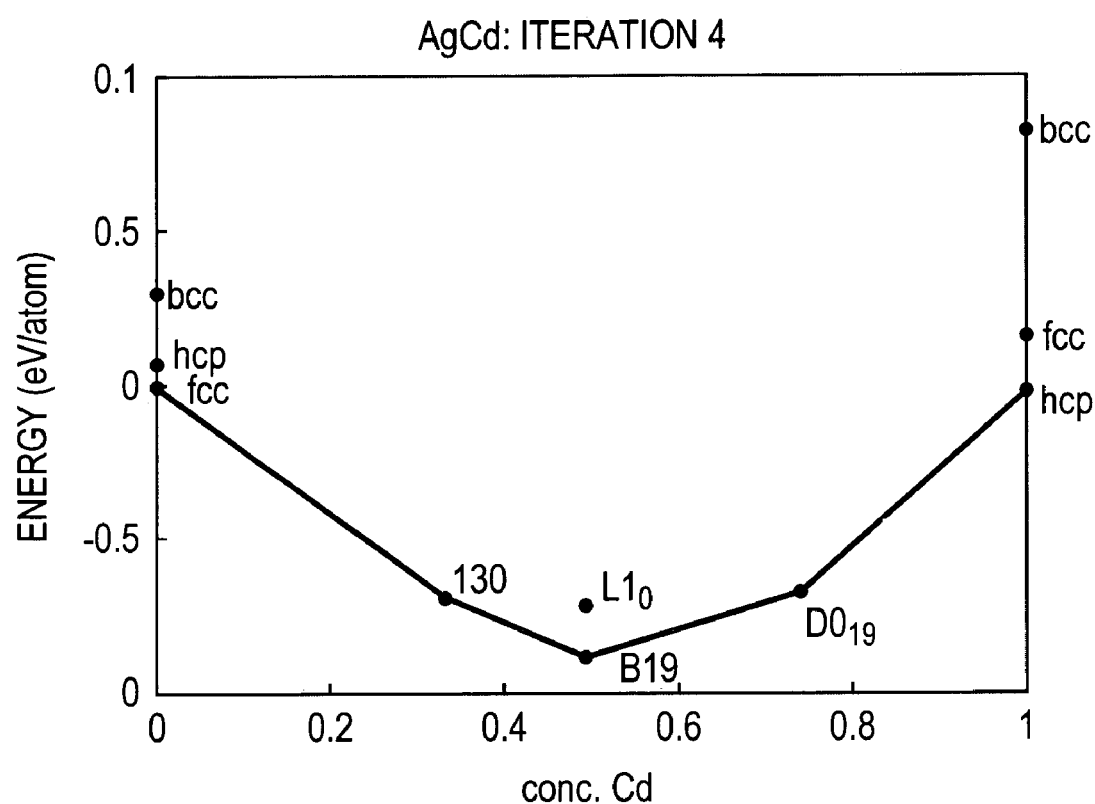
FIG. 3 shows the mixing energies as predicted by the algorithm for the Ag—Cd system at iteration 4, according to principles of the invention.

With the energy of structure "130" calculated the correlation with the database can be made better and the PLS prediction improved. This leads to a more accurate prediction of the energies for all the structures in the database. In the next iteration, the algorithm predicts that B19 will be a stable structure, as shown in FIG. 3.

Figure 4:
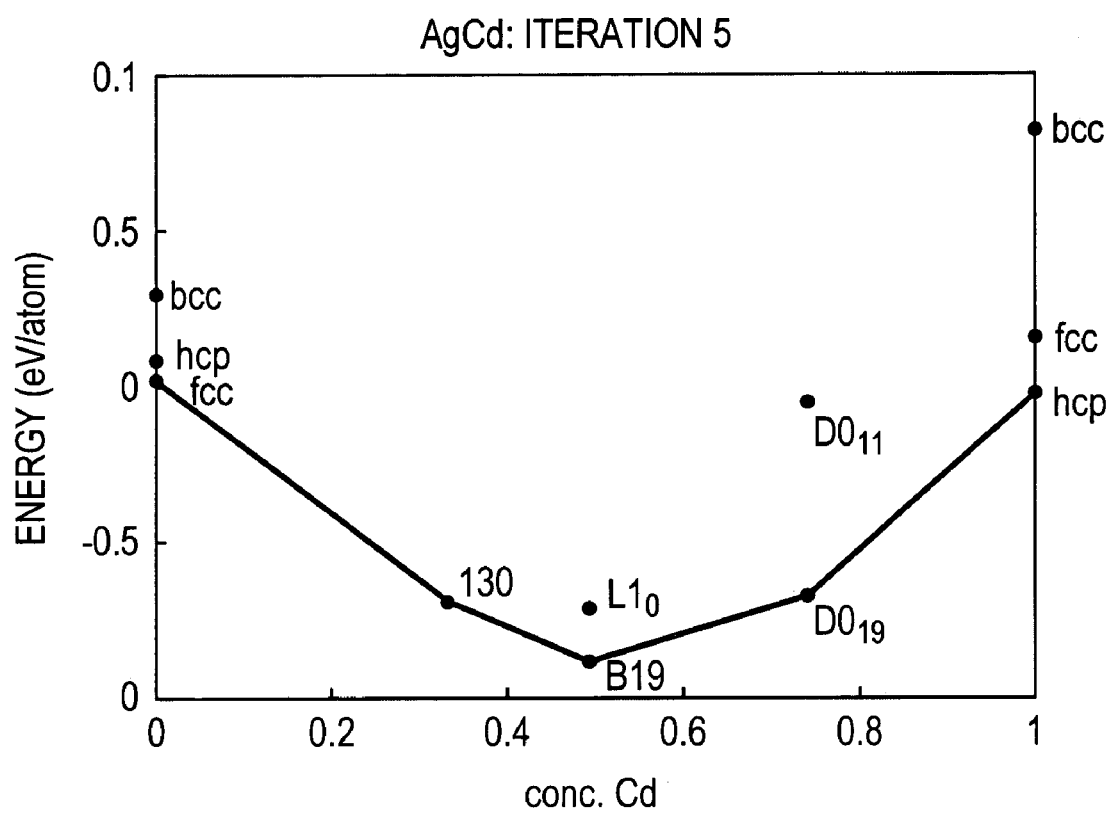
FIG. 4 shows the mixing energies as predicted by the algorithm for the Ag—Cd system at iteration 5, according to principles of the invention.

At each iteration of this algorithm, the energy of a new structure is calculated based on the method's suggestion. If after the PLS prediction, there is no new stable structure suggested, the structure which is predicted closest to the convex hull is calculated. For example, in Iteration 5, the energies and convex hull in FIG. 4 is obtained. Since the ground states are the same as in FIG. 3, the structure $C_{Cd}=0.75$ is taken as the next structure to compute as it is closest to the hull.

Figure 5:
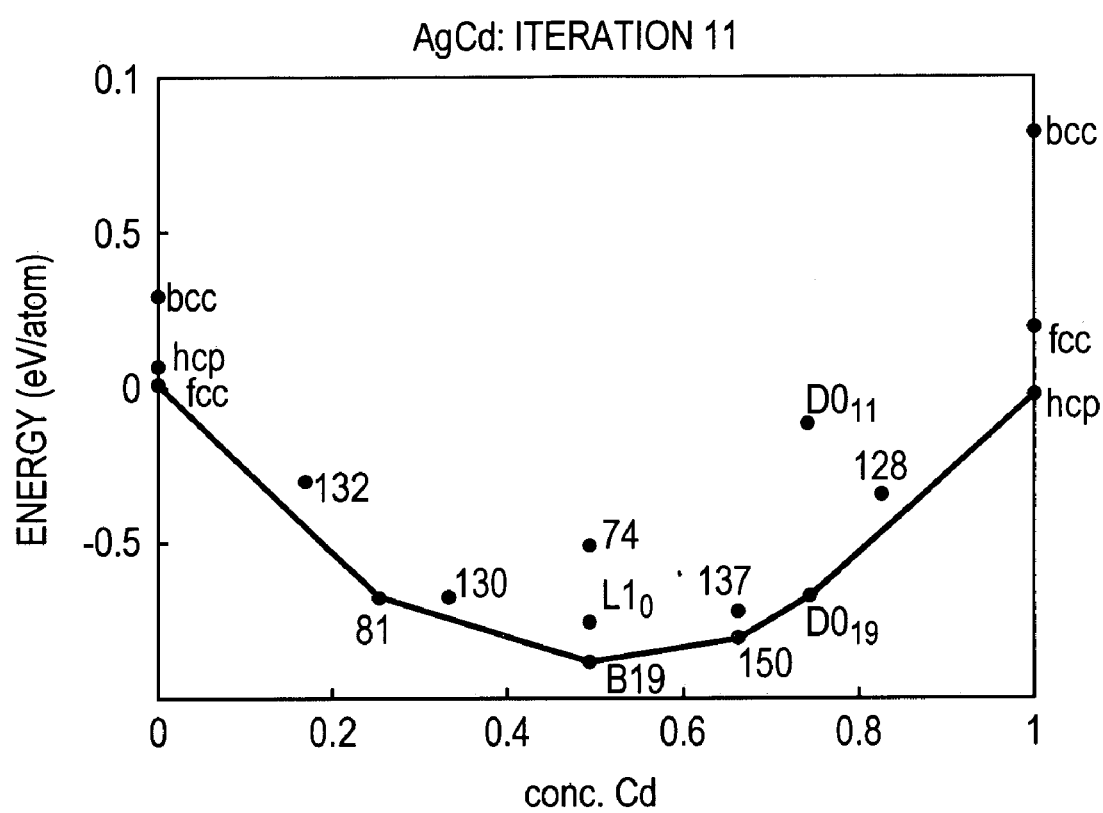
FIG. 5 shows the mixing energies as predicted by the algorithm for the Ag—Cd system at iteration 11, according to principles of the invention.

FIG. 5 shows the ground state hull after 11 iterations. At this point a total of 16 energies have been calculated (10 alloy structures and 6 elements).

Figure 6:
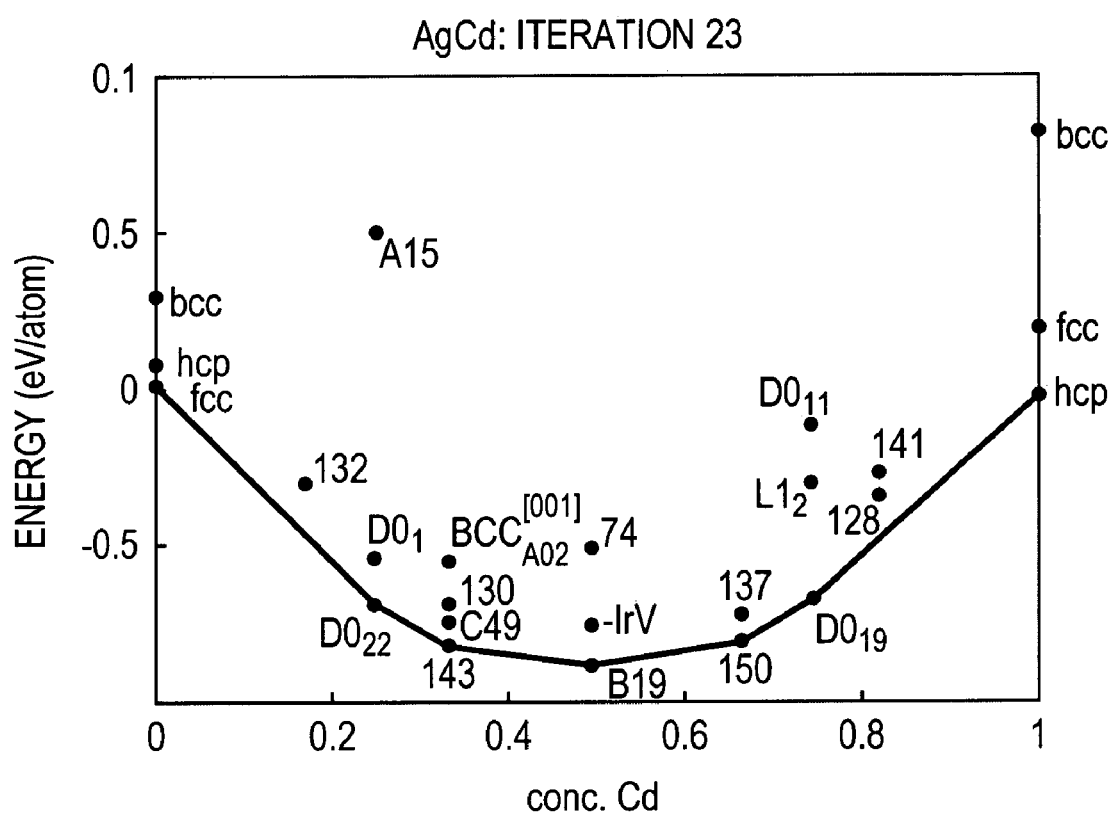
FIG. 6 shows the mixing energies as predicted by the algorithm for the Ag—Cd system at iteration 23, according to principles of the invention.

This iterative scheme can be continued. At each iteration a new candidate ground state is suggested, which is then calculated. Once the energy of this structure is available the PLS prediction can be improved, which leads to the next iteration. In this example, 23 iterations were performed. FIG. 6 shows the ground states after 23 iterations. At this point, the algorithm has found all the ground states that it can find, based on the database used.

Figure 7:
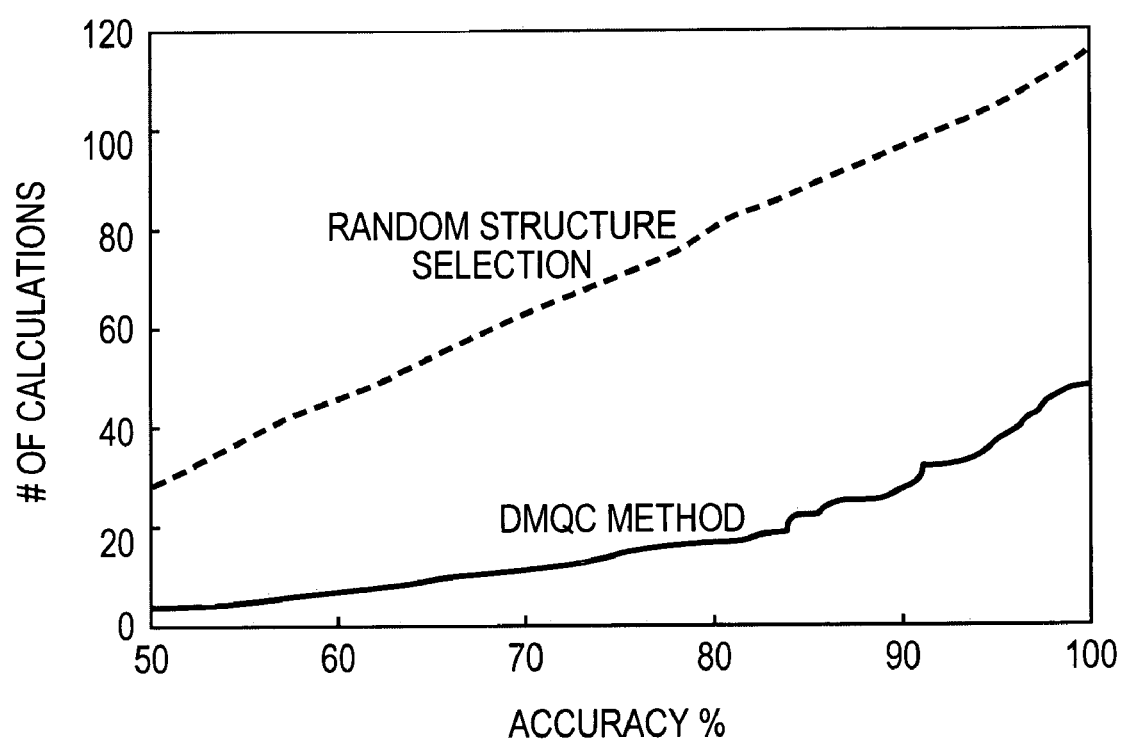
FIG. 7 shows the average number of calculated energies needed (averaged over all the predicted systems) as a function of the accuracy required, according to principles of the invention.

This prediction iteration can be performed on all the systems in the database. To "predict: each system, it is removed from the database and PLS is applied to the remaining database. FIG. 7 shows the average number of calculated energies needed (averaged over all the predicted systems) as a function of the accuracy required. Ninety percent accuracy can be achieved with on average 26 structural energy calculations. This is a significant improvement over randomly picking structures.

EXAMPLE 3

Combining Experimental and Calculated Data in Structure Search Algorithm

In this example we show how information contained within an experimental database of crystal structures can be combined with calculated energies of structures when performing a search for remaining, as yet unknown, stable structures in a materials system of interest. This method suggests the best structures for further calculation based upon what is known from previous calculations and the information in the experimental database.

Figure 8:
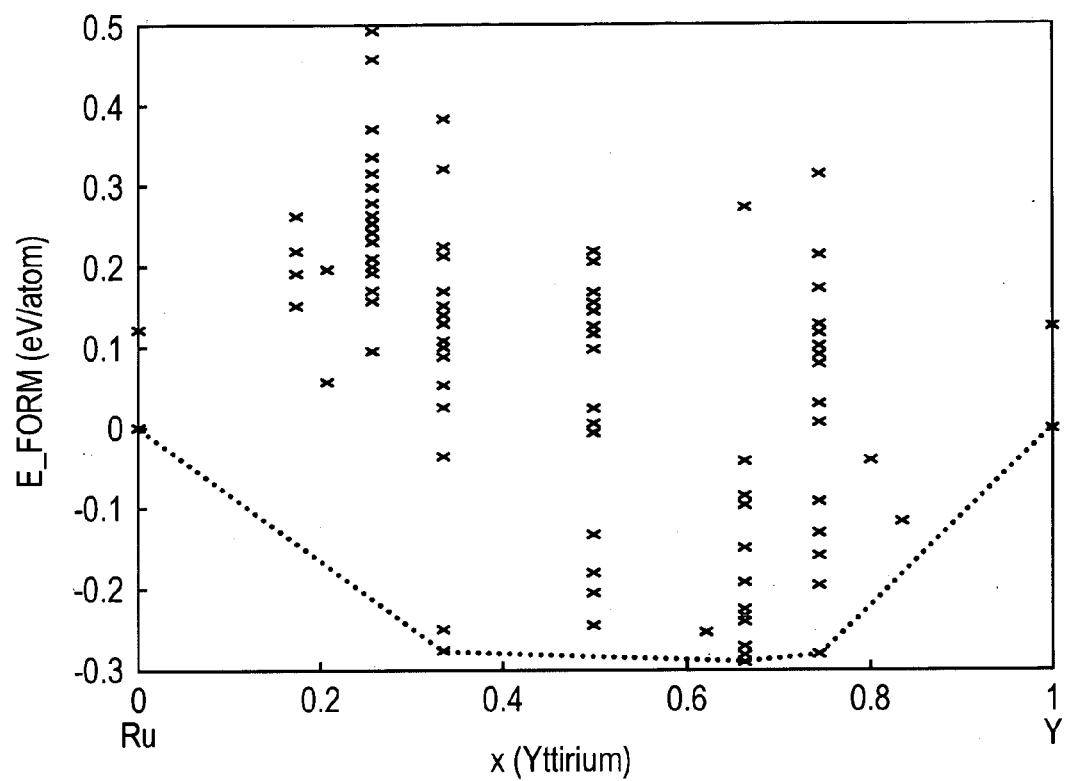
FIG. 8 shows a convex hull calculated for the Ru—Y alloy system using 174 different crystal structures, according to principles of the invention.

Method:

Defining "known" information:

After a series of calculations have been conducted (using a pre-defined set of structures), a ground state convex hull can be constructed for the alloy system of interest. For example, FIG. 8 shows a convex hull calculated for the Ru—Y alloy system using 174 different crystal structures.

The convex hull is the T=0 boundary condition for the alloy phase diagram. The vertices of the convex hull are the stable phases at T=0. In this example the calculated energies indicate that structures C14 at x=0.33, C16 at x=0.66, and $D0_{11}$ at x=0.75 are stable compounds. Experimentally, $D0_{11}$ at x=0.75, C14 at x=0.33, and three others not yet calculated are observed, but C16 at x=0.66 is not. The objective of this example is to suggest other structures that may be stable in this system. To define the set of "known" events for this alloy system we will take the intersection of events defining the calculated and experimental results (i.e., $D0_{11}$ and C14 along with the pure elements hcp-Ru, and hcp-Y). This set of events represents the knowledge that is consistent between the calculated and experimental results. Table V illustrates the data obtained from the experimental database, the calculations, and the events relevant to our algorithm.

TABLE V

Events common to- vs. unique to- experimental and calculated data

| | Experiment | Calculation |
| --- | --- | --- |
| Intersection of events | Hcp-Ru | Hcp-Ru |
| | Hcp-Y | Hcp-Y |
| | $D0_{11}$ | $D0_{11}$ |
| | C14 | C14 |
| (union minus intersection) of events | $C_2Mn_5$ | C16 |
| | $Ru_{25}Y_{44}$ | |
| | $Er_3Ru_2$ | |

Calculating Candidate Structure Lists:

To proceed further, our algorithm next finds the set of most likely stable compounds to calculate. Our decision regarding the best candidate structure to calculate will be made based upon a ranking of probabilities similar to those calculated in Example 1. To construct an ordered list of "best" candidates, we will calculate $p(\beta(c_i)|\alpha(c_1), \ldots, \alpha(c_n))$ for all structures $\{\beta(c_i)\}$ appearing at compositions other than (x=0.0, x=0.33, x=0.75, and x=1.0). The set of events common to the experimental and calculated information is taken as the known information upon which we will condition our probabilities. In particular, $(\alpha(c_1), \ldots, \alpha(c_n))$, comprises $D0_{11}$ and C14, hcp-Ru, and hcp-Y.

The cumulant expansion technique described in Example 1 is used to calculate the set of probabilities $\{p(\beta(c_i)|\alpha(c_1), \ldots, \alpha(c_n))\}$, and the experimental database is used for the counts needed to calculate the quantities $p(\beta(c_i)|\alpha(c_j))$ and $p(\beta(c_i))$. Candidate structures are ordered at each composition by their respective values of $p(\beta(c_i)|\alpha(c_1), \ldots, \alpha(c_n))$. The actual order in which calculations are conducted might be based on an estimate for the computational time requirement for descending down each list or the relative values of $\{p(\beta(c_i)|\alpha(c_1), \ldots, \alpha(c_n))\}$.

Figure 9:
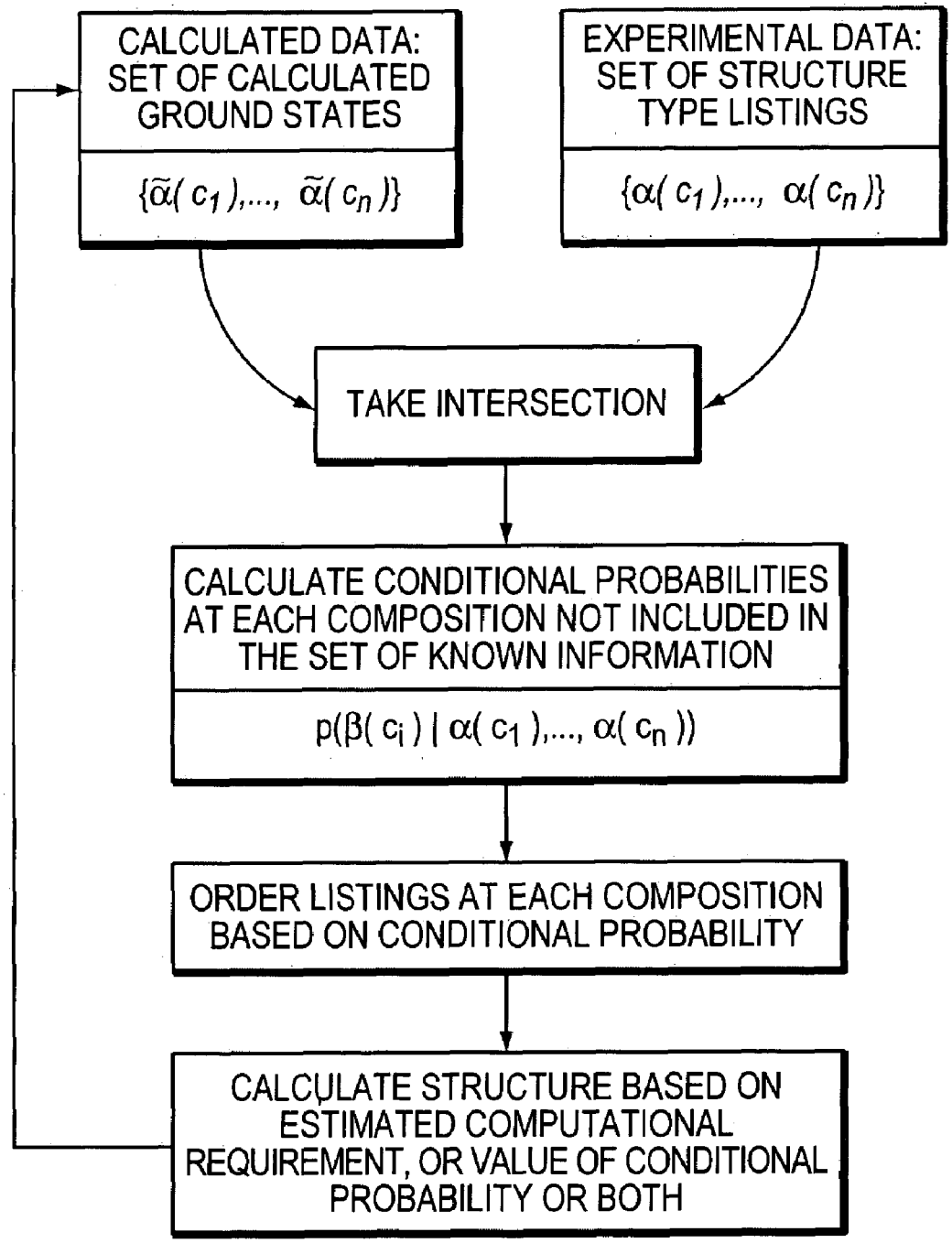
FIG. 9 is a flow diagram showing an exemplary method of calculation, according to principles of the invention.

Calculation Followed by Update:

After calculating the best candidate structure, additional agreements/disagreements might be found between the calculated and experimental results. Therefore, what constitutes the known information for the next iteration would be updated for subsequent calculations. This process is shown schematically in FIG. 9, a flow diagram.

Intersection of Events Yields the Null Set {}:

If the intersection of experimental and calculated results yields the null set, a start-up set of candidates will need to be generated. To address this situation, the search could be initiated in the following manner.

First, two sets of candidate lists are generated, one using only the experimental results as known information, and the other using only the calculated results. Next, the lists are merged, adding the probabilities for each structure type. Finally, candidate lists at compositions common to both sets of lists (i.e. compositions which do not have a listing in either the experimental or calculated results) are renormalized and new structures are then calculated based upon their ranking.

Results:

As stated above, the experimental and calculated data for this system agree on the stability of $D0_{11}$, C14, and elements hcp-(Ru and Y). The experimental data and calculations differ in that structures C2Mn5, Ru25Y44, and Er3Ru2 are found experimentally and calculation indicates that C16 is stable. In what follows we will attempt to predict the set of candidate structures to calculate at x=0.714, x=0.638, and x=0.60 conditioned on the knowledge of hcp-(Ru and Y), $D0_{11}$, and C14. In principle, candidate structure lists would be made at all compositions other than x={0.0, 0.33, 0.75, 1.0}, but the results at x={0.60, 0.638, 0.714} are of interest as compounds are known to appear experimentally (serving as our reference). Shown below in Tables VI, VII, and VIII are the rankings of candidate structures based on frequency of occurrence and the method developed in Example 1.

TABLE VI

Candidate Structure list at x = 0.714

| Str_type(expt.) Mn5C2 Ranking | comp 0.71400 Cumulant | Value | Freq | Value |
|---|---|---|---|---|
| 1 | Mn5C2 | 0.99976 | Mn5C2 | 34 |
| 2 | Sc11Ir4 | 0.00013 | Dy2.12Pd0.88 | 7 |
| 3 | Dy2.12Pd0.88 | 0.00004 | Ce2Sn5 | 5 |
| 4 | Co2Al5 | 0.00003 | | 5 |

TABLE VII

Candidate structure list for x = 0.638

| Str_type(expt.) Y44Ru25 Ranking | comp 0.63800 Cumulant | Value | Freq | Value |
|---|---|---|---|---|
| 1 | Mn5Si3 | 0.98836 | Mn5Si3 | 118 |
| 2 | Cr5B3 | 0.00375 | Pu3Pd5 | 33 |
| 3 | Y44Ru25 | 0.00369 | W5Si3 | 28 |
| 4 | Pu3Pd5 | 0.00181 | Cr5B3 | 28 |
| 5 | | | Pu5Rh3 | 14 |
| 6 | | | Tm3Ga5 | 11 |
| 7 | | | Y3Ge5 | 10 |
| 8 | | | Y5Bi3 | 9 |
| 9 | | | Yb5Sb3 | 7 |
| 10 | | | Rh5Ge3 | 6 |
| 11 | | | Y44Ru25 | 6 |
| 12 | | | | |

TABLE VIII

Candidate structure list for x = 0.60

| Str_type(expt.) Er3Ru2 Ranking | comp 0.60000 Cumulant | Value | Freq | Value |
|---|---|---|---|---|
| 1 | Er3Ru2 | 0.54381 | (Cr0.49Fe0.51) | 24 |
| 2 | Y3Rh2 | 0.11078 | Er3Ni2 | 21 |
| 3 | (Cr0.49Fe0.51) | 0.09791 | U3Si2 | 16 |
| 4 | U3Si2 | 0.09511 | Y3Rh2 | 11 |
| 5 | | | Gd3Ga2 | 11 |
| 6 | | | Ni2Al3 | 10 |
| 7 | | | Ca16Sb11 | 10 |
| 8 | | | Cu5Zn8 | 6 |
| 9 | | | Zr3Al2 | 6 |
| 10 | | | Zr7Ni10 | 5 |
| 11 | | | Gd3Al2 | 5 |
| 12 | | | Er3Ru2 | 5 |

Although not yet calculated, the structures observed experimentally are likely candidates. At compositions x=0.638 and x=0.60, the cumulant method outperforms (in suggesting the structures observed experimentally) a ranking based on frequency of occurrence. Although the cumulant method does not render $Y_{44}Ru_{55}$ the first candidate to calculate, the method does move $Y_{44}Ru_{55}$ up the candidate list from position 11 to position 3. Furthermore, the relative probabilities given for structures at x=0.714 suggest Mn5C2 as the best candidate by a large factor. In contrast, the relative frequency of occurrences for structures at x=0.714 do not favor Mn5C2 by as large a factor.

EXAMPLE 4

Prediction of Melting Temperatures of Alloys

It is also possible to use the methods described herein to predict materials attributes or features other than structure. In this example we build an algorithm that can estimate the melting temperature of an alloy.

Experimental melting data on melting points is extracted from published phase diagrams in Binary Alloy Phase Diagrams (Publisher ASM). We collect, at concentrations 25%, 50%, and 75% the maximum and minimum temperatures for the coexistence of the solid and the liquid phases. This table of melting data is given in Table IX. Also, we include the maximum and minimum melting temperature of the alloy in all its concentration range. The formation melting temperature, $T_f$, is defined as the difference between the melting temperature and the weighted average of the pure elements melting point, with the concentrations as weights. For each alloy and concentration, we regress Tf with the coefficients given by PLS. The absolute error is defined as $$dT_f = T_f(\text{predicted}) - T_f,$$

and prediction relative error is given by $$\epsilon = dT_f / T_{melting}.$$

Finally, we average the error over all the alloys and we obtain the RMS error of the melting temperature prediction. Because the RMS error is the relative deviation normalized over the melting temperature, the precision of the regression tends to be overestimated. We report the RMS error for all the temperatures, and for the maximum and the minimum temperatures. Table X is a listing of the average prediction error for the formation melting temperature (as defined before), the minimum and maximum melting temperature.

TABLE IX

| $c_b$ alloy | 0% $T_A$ (°C.) | 25% $T_{low}$ (°C.) | 25% $T_{high}$ (°C.) | 50% $T_{low}$ (°C.) | 50% $T_{high}$ (°C.) | 75% $T_{low}$ (°C.) | 75% $T_{high}$ (°C.) | 100% $T_B$ (°C.) | $T_{min}$ (°C.) | $c_b^{T_{min}}$ | $T_{max}$ (°C.) | $c_b^{T_{max}}$ |
|---|---|---|---|---|---|---|---|---|---|---|---|---|
| AgCd | 951 | 830 | 855 | 630 | 710 | 450 | 530 | 321 | 321 | 1.00 | 981 | 0.00 |
| AgMg | 961 | 790 | 830 | 820 | 820 | 494 | 570 | 650 | 472 | 0.83 | 961 | 0.00 |
| MoAg | 2623 | 958 | 2310 | 958 | 2200 | 958 | 2075 | 951 | 951 | 1.00 | 2623 | 0.00 |

TABLE IX-continued

| $c_b$ alloy | 0% $T_A$ (° C.) | 25% $T_{low}$ (° C.) | 25% $T_{high}$ (° C.) | 50% $T_{low}$ (° C.) | 50% $T_{high}$ (° C.) | 75% $T_{low}$ (° C.) | 75% $T_{high}$ (° C.) | 100% $T_B$ (° C.) | $T_{min}$ (° C.) | $c_b^{Tmin}$ | $T_{max}$ (° C.) | $c_b^{Tmax}$ |
|---|---|---|---|---|---|---|---|---|---|---|---|---|
| MoCd | 2623 | 321 | 767 | 321 | 757 | 321 | 767 | 321 | 321 | 1.00 | 2623 | 0.00 |
| MoPd | 2623 | 1755 | 2270 | 1755 | 1850 | 1680 | 1710 | 1555 | 1700 | 0.54 | 2623 | 0.00 |
| MoRh | 2623 | 1940 | 2170 | 2020 | 2050 | 2015 | 2035 | 1963 | 1940 | 0.39 | 2623 | 0.00 |
| MoRu | 2623 | 2040 | 2180 | 1970 | 2040 | 2180 | 2210 | 2334 | 1955 | 0.42 | 2623 | 0.00 |
| MoTc | 2623 | 2135 | 2320 | 2027 | 2230 | 2080 | 2100 | 2204 | 2027 | 0.55 | 2623 | 0.00 |
| NbMo | 2459 | 2483 | 2515 | 2515 | 2560 | 2565 | 2595 | 2623 | 2469 | 0.00 | 2623 | 1.00 |
| NbPd | 2459 | 1380 | 2180 | 1520 | 1550 | 1625 | 1625 | 1555 | 1520 | 0.47 | 2469 | 0.00 |
| NbRh | 2469 | 1663 | 1860 | 1550 | 1560 | 1910 | 1940 | 1953 | 1502 | 0.45 | 2469 | 0.00 |
| NbRu | 2469 | 1930 | 1950 | 1942 | 1942 | 1360 | 1975 | 2334 | 1774 | 0.65 | 2469 | 0.00 |
| PdAg | 1555 | 1390 | 1445 | 1285 | 1330 | 1130 | 1170 | 961 | 961 | 1.00 | 1555 | 0.00 |
| RhAg | 1963 | 1900 | 951 | 1900 | 961 | 1900 | 961 | 961 | 961 | 1.00 | 1953 | 0.00 |
| RhPd | 1963 | 1860 | 1900 | 1730 | 1820 | 1620 | 1680 | 1555 | 1555 | 1.00 | 1963 | 0.00 |
| RuPd | 2334 | 1583 | 2100 | 1583 | 1980 | 1553 | 1800 | 1555 | 1555 | 1.00 | 2334 | 0.00 |
| RuRh | 2334 | 2240 | 2290 | 2110 | 2160 | 2040 | 2060 | 1963 | 1963 | 1.00 | 2334 | 0.00 |
| StAl | 1541 | 945 | 1140 | 1150 | 1300 | 655 | 1320 | 650 | 660 | 1.00 | 1541 | 0.00 |
| TcPd | 2155 | 1850 | 2100 | 1700 | 1900 | 1650 | 1680 | 1555 | 1555 | 1.00 | 2155 | 0.00 |
| TcRh | 2155 | 2120 | 2150 | 2100 | 2120 | 2050 | 2100 | 1953 | 1963 | 1.00 | 2155 | 0.00 |
| TiAg | 1670 | 1020 | 1530 | 1020 | 1455 | 1020 | 1330 | 961 | 961 | 1.00 | 1670 | 0.00 |
| TiMo | 1670 | 1810 | 1950 | 2030 | 2180 | 2310 | 2400 | 2623 | 1671 | 0.00 | 2623 | 1.00 |
| TiPd | 1670 | 1150 | 1280 | 1400 | 1400 | 1490 | 1530 | 1555 | 1120 | 0.32 | 1670 | 0.00 |
| TiRh | 1670 | 1300 | 1320 | 1940 | 1940 | 1750 | 1780 | 1963 | 1280 | 0.29 | 1963 | 1.00 |
| TiRu | 1670 | 1575 | 1610 | 2130 | 2130 | 1825 | 1860 | 2334 | 1575 | 0.25 | 2334 | 1.00 |
| TiZr | 1670 | 1560 | 1580 | 1550 | 1560 | 1690 | 1720 | 1855 | 1540 | 0.39 | 1855 | 1.00 |
| YAg | 1522 | 385 | 980 | 835 | 1160 | 900 | 940 | 961 | 799 | 0.88 | 1522 | 0.00 |
| YMo | 1522 | 1430 | 1780 | 1430 | 2080 | 1430 | 2380 | 2623 | 1430 | 0.10 | 2623 | 1.00 |
| YNb | 1522 | 1470 | 2000 | 1470 | 2400 | 1470 | 2400 | 2469 | 1470 | 0.06 | 2469 | 1.00 |
| YPd | 1522 | 907 | 907 | 1385 | 1440 | 1700 | 1700 | 1555 | 907 | 0.25 | 1700 | 0.75 |
| YRh | 1522 | 1200 | 1300 | 1500 | 1540 | 1470 | 1520 | 1953 | 1150 | 0.20 | 1963 | 1.00 |
| YRu | 1522 | 1250 | 1300 | 1350 | 1750 | 1840 | 1900 | 2334 | 1030 | 0.15 | 2334 | 1.00 |
| YZr | 1522 | 1360 | 1390 | 1360 | 1380 | 1350 | 1550 | 1855 | 1360 | 0.40 | 1855 | 1.00 |
| ZrAg | 1855 | 1190 | 1350 | 1136 | 1160 | 940 | 1120 | 961 | 940 | 0.97 | 1855 | 0.00 |
| ZrMo | 1855 | 1540 | 1700 | 1550 | 1600 | 1380 | 2220 | 2623 | 1550 | 0.45 | 2623 | 1.00 |
| ZrNb | 1855 | 1740 | 1750 | 1850 | 1930 | 2090 | 2220 | 2469 | 1740 | 0.21 | 2469 | 1.00 |
| ZrPd | 1855 | 1030 | 1030 | 1030 | 1600 | 1390 | 1780 | 1555 | 1030 | 0.25 | 1855 | 0.00 |
| ZrRh | 1855 | 1070 | 1130 | 1910 | 1910 | 1900 | 1930 | 1963 | 1070 | 0.23 | 1963 | 1.00 |
| ZrRu | 1855 | 1240 | 1500 | 2130 | 2130 | 1715 | 1780 | 2334 | 1240 | 0.21 | 2334 | 1.00 |

TABLE X

Figure 10:
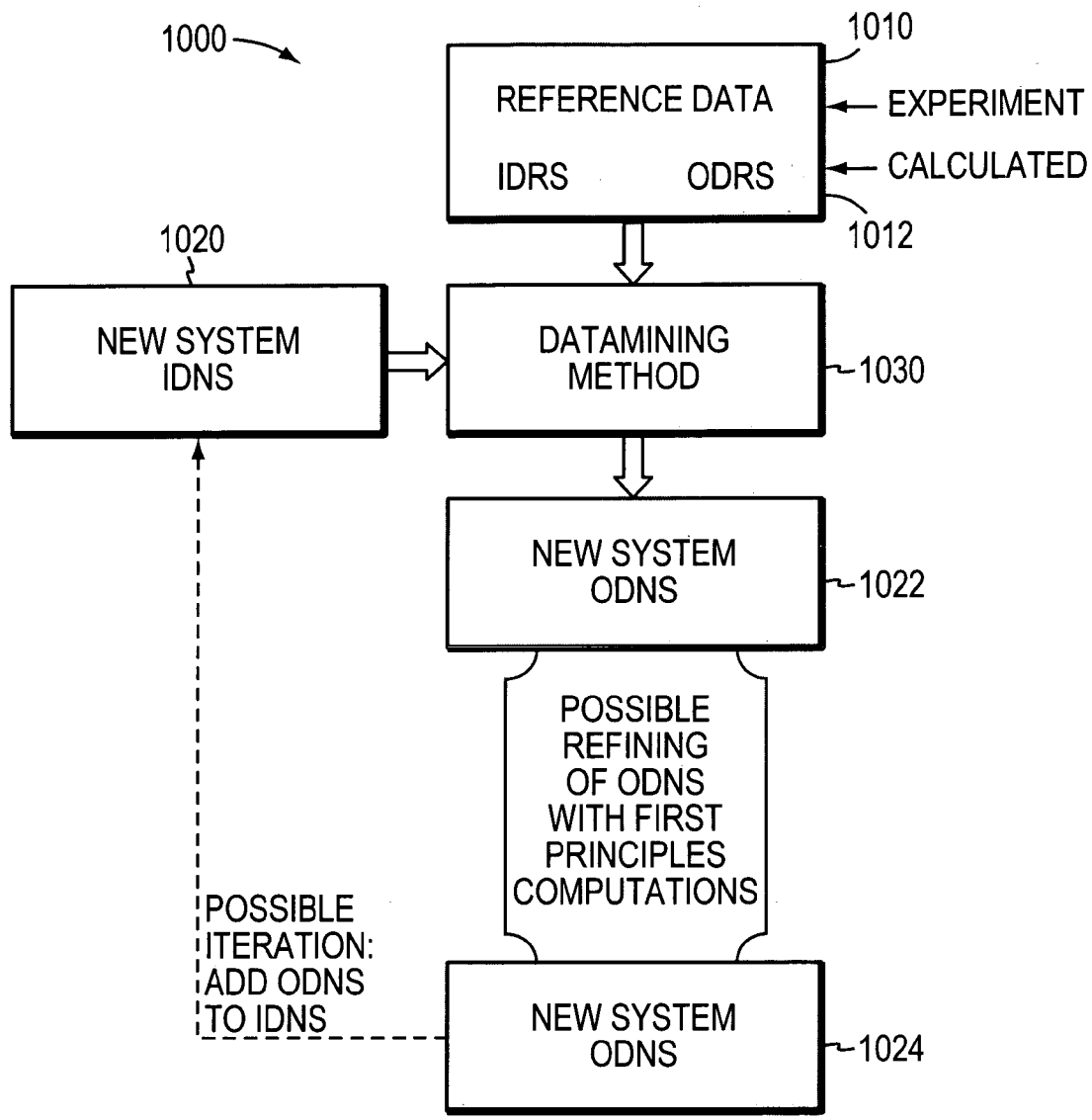
FIG. 10 is a high level flow diagram showing the relationships between reference data, new system data and a data mining method according to principles of the invention.

Lens-like systems predicted with lens-like systems $RMS_c[T] = 12\%$    $RMS_c[T_{min}] = 19\%$    $RMS_c[T_{max}] = 14\%$
Non-Lens-like systems predicted with non-lens-like systems:

$RMS_c[T] = 12\%$    $RMS_c[T_{min}] = 15\%$    $RMS_c[T_{max}] = 18\%$
Lens-like system predicted with all the systems $RMS_c[T] = 15\%$    $RMS_c[T_{min}] = 19\%$    $RMS_c[T_{max}] = 19\%$
Non-Lens-like system predicted with all the systems $RMS_c[T] = 11\%$    $RMS_c[T_{min}] = 13\%$    $RMS_c[T_{max}] = 16\%$
All the systems predicted with all the systems $RMS_c[T] = 12\%$    $RMS_c[T_{min}] = 15\%$    $RMS_c[T_{max}] = 17\%$ Data Mining: Organization of Methods FIG. 10 is a high level flow diagram 1000 showing the relationships between reference system data 1010, 1012, new system data 1020, 1022, 1024, and a data mining method 1030 according to principles of the invention. In one embodiment, the invention can be described with regard to the input data for the reference system (IDRS) 1010, output data for the reference system (ODRS) 1012, input data for new system (IDNS) 1020, and output data for the new system (ODNS) 1022, 1024. An algorithm that learns, for example a neural network, seeks a correlation between IDRS and ODRS. The system then applies the correlation to the IDNS to predict unknown information for the new system (ODNS). In some embodiments, systematically stating the nature of this data makes clear the distinction between the inventive data mining methods and previous ones.

Data for the Reference System (DRS)

These are the data types which are used to build or discover a correlation. In some embodiments, these data can be referred to as a "training set" or "reference data." One can distinguish Input DRS (IDRS) and Output DRS (ODRS). These sets can be distinct (e.g., their intersection is the null set) or they can overlap (e.g., their intersection is a set having at least one member). In one exemplary embodiment, involving Pauling files, the ODRS and IDRS are the same set and constitute the experimentally observed stable crystal structures as function of composition for a large number of alloys. In the PLS approach, these data are the computed energies of a set of structures, which are not limited to only the stable structures, in a series of reference alloys. For Pettifor maps, the IDRS are the ordinal numbers that represent elements in the Periodic Table (e.g., the Mendeleyev numbers of the elements) in an alloy and the ODRS is the crystal structure at a particular composition.

Inputs for the New System (IDNS)

This is the data that is available (or generated) for the new system and on which a prediction is based. Note that the kinds of data represented by an IDNS needs to be a subset of the kinds of data represented by the IDRS. For example, if the IDRS includes crystal structure data as a function of composition, temperature, and pressure, then the IDNS could be crystal structure data as a function of one or more of composition, temperature, and pressure. If the IDNS is not a subset of the IDRS, a correlation can not be built. For example, if the IDRS is structure data as a function of composition and temperature, while the IDNS is structure data as a function of composition and pressure, relationships that exist for the IDRS may not be informative for studying the IDNS.

Output Data Predicted for New System (ODNS)

The output data for the new system can be any type of information that is present in the ODRS. In some embodiments, in which there is overlap between the information present in the ODRS and the IDRS, an iterative method can be built. In the iterative method, some portion of the predicted data (output data) can be used as input for the next iteration. Note, the possibility of iteration when the input and output data sets include information of the same type applies to all of the techniques discussed herein.

Methods Used to Make the Prediction

The method is shown schematically in FIG. 10. Different embodiments of the method will be presented as examples.

EXAMPLE 1

Predicting Structure Based Solely On First Principles Data

In this example, the IDRS and the ODRS represent calculated energies of structures at various compositions in a series of binary alloy systems. One can define at least one IDNS as the energy of at least one structure in a new alloy. For this example, the ODNS is calculated and includes a set of energies of all structures in the new alloy system. In such an embodiment, iteration is possible, since ODRS is a subset of IDRS.

EXAMPLE 2

Predicting Structures in a New System Based on the Knowledge That Some Structures are Present, and Given an Experimental Database of Stable Structures In this embodiment, the IDRS and the ODRS represent a set of stable structures as a function of composition for all materials in the experimental database. In this example, the IDNS represents one or more known stable structures in a new system (e.g., a system that is of interest, or that is the subject of a technical investigation). The ODNS represents one or more candidate stable structures in the new system. Iteration is possible in this case in many ways. In one embodiment, one can use an "Expectation Maximization" algorithm wherein the calculated distribution is used to update the input data and the computation is iterated until convergence to within a desired error amount occurs. In another embodiment, one can use first principles computations to calculate one or more likely structures and add the result to the IDNS.

EXAMPLE 3

Predicting Melting Temperature from the Cohesive Energy of an Alloy

In this example, the IDRS represents at least one cohesive energy of at least one structure. In some embodiments, the IDRS includes a plurality of data for a series of structures. In this embodiment, the ODRS represents one or more melting points, one melting point corresponding to each structure in the IDRS. In this embodiment, the IDNS represents a cohesive energy of a new structure, and the ODNS represents a predicted melting point of the new structure. Because the information represented by the inputs (IDRS and IDNS) are not the same type of information as the outputs (ODRS and ODNS), that is, a cohesive energy and a melting point do not represent values for the same thing, no iteration is possible in this case. However, as more data appears in the IDRS and ODRS, e.g., new calculated information for a previously unknown structure is obtained, and is added to the IDRS and ODRS so as to augment the previous data contained therein, the precision of the computational procedure (that is, the data mining engine, or the algorithmic process for performing the calculation) can increase because the added data permits refinement of the computational procedure.

EXAMPLE 4

Prediction of Crystal Structure or Structure Descriptors

A crystal structure can be described in many ways. Examples of structural descriptors include: a prototype, for example a commonly used chemical name as structure descriptor such as NaCl; a Strukturbericht notation; a combination of space group, unit cell and coordinate data; a structure type; a Pauling symbol; and a lattice type. Most of these are complete descriptions, i.e. they characterize the structure uniquely. Structures can also be partially described, for example by structure descriptors: Coordination number, pair correlation function, space group, lattice type, short-range order parameter, one or more lattice parameters. These all describe a structure partially, but not completely.

We turn now to an example in which the goal is complete structure prediction (as for example by prototype). However, one can also predict a structure partially, by using various of the structure descriptors enumerated hereinabove. The general case for an ODNS is a generic property of the predicted phase/crystal structure, be it a full or partial structural descriptor, susceptibility, or bound on its stability.

Before presenting an example, we will indicate how a prior art predictor of structure can be understood in the present formalism. Consider a Pettifor map. A Pettifor map is constructed at a fixed composition (e.g. AB or $A_2B$, or $A_3$, etc.). The IDRS represents the Mendeleyev number of two or more elements in a known material at the composition of the Pettifor map, and the_ODRS represents the crystal structure of the known material. For the new system, the IDNS represents the Mendeleyev numbers of the elements present in the material of interest, and the_ODRS represents the predicted crystal structure of the material of interest at the composition of the Pettifor map. In such a system, no iteration is possible and in a Pettifor map of given composition, no information from other compositions (besides the trivial elemental ones) is used to improve the prediction. In general, for prior art systems that rely on structure maps, it appears that the following limiting attributes are common. The IDNS comprises elemental data, such as ionic size, electronegativity, pseudopotential radius, and electron per atom ratio, but the IDNS does not include or provide information about crystal structure stability. In general, the ODRS is the stable crystal structure at the composition for which one is trying to make the prediction (generally at a defined temperature, such as room temperature or 20° C.). No information about crystal structure stability is used at the composition of interest and at other compositions. In general, only information about known materials and structures is used. The inventors are unaware of any such system that uses computed ODRS. In general, the structure assigned in such a mapping analysis is by comparing the nearest chemical systems in the map, and deducing from their structures which is the most likely structure. No iteration of the output data or results is possible in such mapping systems.

In contradistinction to prior art mapping systems, the systems and methods of the invention provide IDRS and ODRS that contain crystal structure information from multiple compositions in a given data set. According to principles of the invention, one can build (or identify) correlations between information (such as crystal structure stability) across compositions, and relate it not only to information about the elements (as is the case for the previous schemes), but to information about the relative stability of different crystal structures, and/or the thermal behavior of crystal structures of specific compositions, such as phase transitions and/or stability of a given structure as a function of temperature.

Furthermore, in systems and methods of the invention, one can establish or identify correlations between a property of the structure of a new system (e.g., a property as ODNS that is a function of structure) and one or more properties (i.e., ODRS) of other compounds in the same alloy system (e.g., reference systems in the same alloy system). The systems and methods of the invention provide a general framework through which correlations (and anti-correlations) can be established and used. By comparison, what has been done thus far is a limiting case of the systems and methods of the invention, namely, the case where IDNS represents only element data. Furthermore, because in the systems and methods of the invention, there are cases where IDRS data is the same type as ODRS data, one can iterate and at each step improve the prediction in the inventive system. As another benefit, the systems and methods of the invention can mix computed stability data and experimentally obtained data.

Structure parameters include but are not limited to structure type (for example using a chemical compound descriptor such as NaCl cubic structure), Pearson symbol, Pauling symbol, space group, lattice type, order parameter, coordination number, and lattice parameters. Phase transitions can include but are not limited to transitions that occur with changes in temperature, transitions that occur with changes in pressure and changes that occur with changes in composition. Electronic, magnetic, photonic and thermodynamic properties include but are not limited to conductivity, mobility (such as mobility of electrical charge, of ions, and of features such as phonons), carrier concentration, energy gap (including electronic and photonic band gaps), effective mass, transition temperatures (such a Curie temperature, a semiconductor-to-metal transition temperature, a Neel temperature, a critical temperature for superconductivity), magnetic susceptibility, color, refractive index, permittivity, compressibility, bulk modulus, thermal expansion coefficient, elastic stiffness, hardness, specific heat capacity, density, enthalpy of formation, and entropy of formation.

Until now, the systems and methods of the invention have been used to study materials at low temperatures and pressures. It is believed that the systems and methods of the invention can be used to predict phase transitions. It is also believed that if high temperature and high pressure data are included in the reference data sets, it is possible to predict phase changes with temperature, pressure or composition.

Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

What is claimed is:

1. A method for predicting a property of an inorganic material of interest, comprising the steps of:

for an inorganic reference material:
  selecting an input data set and an output data set wherein said output data set is a subset of said input data set; and
  identifying a computational procedure that generates a member of said output data set when a member of said input data set comprising an initial value of a parameter of said inorganic reference material is used as input;

for an inorganic material of interest different from said inorganic reference material:
  selecting said inorganic material of interest;
  obtaining for said inorganic material of interest an initial value, said initial value being a selected one of a computed initial value and a measured initial value of at least one parameter of said inorganic material of interest;

providing said initial value of said at least one parameter for said inorganic material of interest to said computational procedure;

computing with said computational procedure to obtain a result;

deducing a candidate property of said inorganic material of interest based on said result; and recording on a machine-readable medium said result to predict said property of said inorganic material of interest.

2. The method for predicting a property of an inorganic material of interest of claim 1, further comprising the steps of:

for said inorganic material of interest different from an inorganic reference material:

obtaining for said inorganic material of interest an initial value, said initial value differing from a descriptor of an element present in said inorganic material of interest;

providing said initial value of said at least one parameter for said inorganic material of interest to a computational procedure;

computing with said computational procedure to obtain a result, said computational procedure being a selected one of:

a computation that obtains a relationship between a known structure of at least one known inorganic reference material and a known initial value of a parameter of said at least one known inorganic reference material and that applies said relationship to said initial value of said at least one parameter for said inorganic material of interest, and a computation that compares said initial value of said at least one parameter for said inorganic material of interest with a known value of a corresponding parameter of said at least one known inorganic reference material, and that applies said comparison to a structural parameter of said known reference material;

deducing as a candidate property a structure of said inorganic material of interest based on said result;

whereby data is generated to predict said structure of said inorganic material of interest.

3. The method for predicting a property of an inorganic material of interest of claim 2, wherein said obtaining step includes obtaining an additional initial value of at least one parameter of said inorganic material of interest, said additional initial value comprising a descriptor of an element present in said inorganic material of interest.

4. The method for predicting a property of an inorganic material of interest of claim 2, further comprising the optional step of computing a new parameter value for said candidate structure of said inorganic material of interest.

5. The method for predicting a property of an inorganic material of interest of claim 4, further comprising the optional step of, as necessary, iteratively performing the steps of providing said initial value of said at least one parameter for said inorganic material of interest wherein said new computed parameter is substituted for said initial value, deducing a candidate structure of said inorganic material of interest, and computing yet another new parameter value for said candidate structure.

6. The method for predicting a property of an inorganic material of interest of claim 5, wherein the step of iteratively performing the steps of providing, deducing, and computing is terminated when a metric relating to an incremental change of said parameter of said inorganic material of interest is less than a predefined difference.

7. The method for predicting a property of an inorganic material of interest of claim 2, wherein at least one of said steps of providing, computing, and deducing is performed in a computational system comprising a programmed computer.

8. The method for predicting a property of an inorganic material of interest of claim 7, wherein said computational system comprising a programmed computer further comprises a computer program containing an algorithm.

9. The method for predicting a property of an inorganic material of interest of claim 7, wherein said computational system comprising a programmed computer further comprises a knowledge machine.

10. The method for predicting a property of an inorganic material of interest of claim 2, wherein said inorganic material of interest comprises a plurality of inorganic materials.

11. The method for predicting a property of an inorganic material of interest of claim 2, wherein said inorganic reference material comprises a plurality of materials.

12. The method for predicting a property of an inorganic material of interest of claim 2, wherein said initial value of said inorganic material of interest comprises a plurality of initial values for a plurality of parameters of said inorganic material of interest.

13. The method for predicting a property of an inorganic material of interest of claim 2, wherein said initial value of said parameter of said inorganic reference material comprises a plurality of initial values for a plurality of parameters of said inorganic reference material.

14. The method for predicting a property of an inorganic material of interest of claim 2, wherein said known value of said parameter of said inorganic reference material comprises at least one machine-readable datum.

15. The method for predicting a property of an inorganic material of interest of claim 14, wherein said at least one machine-readable datum comprises an element of a database.

16. The method for predicting a property of an inorganic material of interest of claim 2, wherein said structure is characterized uniquely.

17. The method for predicting a property of an inorganic material of interest of claim 2, wherein said structure is partially described.

18. The method for predicting a property of an inorganic material of interest of claim 17, wherein said structure comprises a selected one of a charge density, a structural property, a parameter of a crystal structure, a parameter of a non-crystalline structure, a symmetry of a structure, a space group, a point group, an electronic structure property, and a quantity calculable from one or more of a quantum-mechanical ground state, a quantum mechanical excited state, and a generalized thermodynamic susceptibility of said inorganic material of interest.

19. The method for predicting a property of an inorganic material of interest of claim 2, wherein the prediction of said structure of said inorganic material of interest comprises a prediction that said inorganic material of interest is not stable under a defined condition.

20. The method for predicting a property of an inorganic material of interest of claim 2, wherein said structure is a function of temperature.

21. The method for predicting a property of an inorganic material of interest of claim 2, wherein said structure is a function of pressure.

22. The method for predicting a property of an inorganic material of interest of claim 2, wherein said structure is a function of volume.

23. The method for predicting a property of an inorganic material of interest of claim 2, wherein said structure is a function of a thermodynamic field or a thermodynamic force.

24. The method for predicting a property of an inorganic material of interest of claim 2, wherein said structure is a function of chemical composition.

25. The method for predicting a property of an inorganic material of interest of claim 2, wherein the step of computing comprises applying a computational method involving a selected one or more of a partial least square (PLS) method, a Principal Component Analysis (PCA) method, a data mining method, a knowledge discovery method, a visualization method, a statistical method, a regression method, a linear regression method, a non-linear regression method, a Bayesian method, a clustering method, a neural network method, a support vector machine method, a decision tree method, and a cumulant expansion.

26. The method for predicting a property of an inorganic material of interest of claim 1, further comprising the optional step of computing a new parameter value for said candidate property of said inorganic material of interest.

27. The method for predicting a property of an inorganic material of interest of claim 26, further comprising the optional step of, as necessary, iteratively performing the steps of providing said initial value of said at least one parameter for said inorganic material of interest wherein said new computed parameter is substituted for said initial value, deducing a candidate property of said inorganic material of interest, and computing yet another new parameter value for said candidate property.

28. The method for predicting a property of an inorganic material of interest of claim 27, wherein the step of iteratively performing the steps of providing, deducing, and computing is terminated when a metric relating to an incremental change of said parameter of said inorganic material of interest is less than a predefined difference.

29. The method for predicting a property of an inorganic material of interest of claim 1, wherein at least one of said steps of providing, computing and deducing is performed in a computational system comprising a programmed computer.

30. The method for predicting a property of an inorganic material of interest of claim 29, wherein said computational system comprising a programmed computer further comprises a computer program containing an algorithm.

31. The method for predicting a property of an inorganic material of interest of claim 29, wherein said computational system comprising a programmed computer further comprises a knowledge machine.

32. The method for predicting a property of an inorganic material of interest of claim 1, wherein said initial value of said parameter for said inorganic material of interest and said initial value of said parameter for said inorganic reference material are parameters that describe a corresponding material feature.

33. The method for predicting a property of an inorganic material of interest of claim 1, wherein said inorganic material of interest comprises a plurality of inorganic materials.

34. The method for predicting a property of an inorganic material of interest of claim 1, wherein said inorganic reference material comprises a plurality of materials.

35. The method for predicting a property of an inorganic material of interest of claim 1, wherein said initial value of said inorganic material of interest comprises a plurality of initial values of said inorganic material of interest.

36. The method for predicting a property of an inorganic material of interest of claim 1, wherein said initial value of said parameter of said inorganic reference material comprises a plurality of initial values for a plurality of parameters of said reference material.

37. The method for predicting a property of an inorganic material of interest of claim 1, wherein said initial value of said parameter of said inorganic reference material comprises at least one machine-readable datum.

38. The method for predicting a property of an inorganic material of interest of claim 37, wherein said at least one machine-readable datum comprises an element of a database.

39. The method for predicting a property of an inorganic material of interest of claim 38, wherein at least one of said initial value of said inorganic material of interest and said predicted property of said inorganic material of interest is added to said database.

40. The method for predicting a property of an inorganic material of interest of claim 1, wherein said property comprises a selected one of an energy, a charge density, a structural property, a parameter of a crystal structure, a parameter of a non-crystalline structure, a symmetry of a structure, a space group, a point group, an optical property, an electro-magnetic property, a mechanical property, a quantum-mechanical property, an electronic structure property, a thermodynamic property, a magnetic property, and a quantity calculable from one or more of a quantum-mechanical ground state, a quantum mechanical excited state, and a generalized thermodynamic susceptibility of said inorganic material of interest.

41. The method for predicting a property of an inorganic material of interest of claim 1, wherein the prediction of said property of said inorganic material of interest comprises a prediction that said inorganic material of interest is not stable under a defined condition.

42. The method for predicting a property of an inorganic material of interest of claim 1, wherein said property is a function of temperature.

43. The method for predicting a property of an inorganic material of interest of claim 1, wherein said property is a function of pressure.

44. The method for predicting a property of an inorganic material of interest of claim 1, wherein said property is a function of volume.

45. The method for predicting a property of an inorganic material of interest of claim 1, wherein said property is a function of a thermodynamic field or a thermodynamic force.

46. The method for predicting a property of an inorganic material of interest of claim 1, wherein said property is a function of chemical composition.

47. The method for predicting a property of an inorganic material of interest of claim 1, wherein the step of computing comprises applying a computational method involving a selected one or more of a partial least square (PLS) method, a Principal Component Analysis (PCA) method, a data mining method, a knowledge discovery method, a visualization method, a statistical method, a regression method, a linear regression method, a non-linear regression method, a Bayesian method, a clustering method, a neural network method, a support vector machine method, a decision tree method, and a cumulant expansion.

* * * * *